US010605811B2

(12) United States Patent
Mansfield et al.

(10) Patent No.: US 10,605,811 B2
(45) Date of Patent: *Mar. 31, 2020

(54) PREDICTIVE BIOMARKERS FOR OVARIAN CANCER

(71) Applicant: VERMILLION, INC., Austin, TX (US)

(72) Inventors: Brian C. Mansfield, Austin, TX (US); Ping F. Yip, Austin, TX (US); Suraj Amonkar, Austin, TX (US); Greg P. Bertenshaw, Austin, TX (US)

(73) Assignee: VERMILLION, INC., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/815,085

(22) Filed: Nov. 16, 2017

(65) Prior Publication Data
US 2018/0074064 A1 Mar. 15, 2018

Related U.S. Application Data

(60) Continuation of application No. 15/041,754, filed on Feb. 11, 2016, now Pat. No. 9,846,158, which is a continuation of application No. 14/172,237, filed on Feb. 4, 2014, now Pat. No. 9,274,118, which is a division of application No. 12/165,240, filed on Jun. 30, 2008, now Pat. No. 8,664,358.

(60) Provisional application No. 61/037,946, filed on Mar. 19, 2008, provisional application No. 60/947,253, filed on Jun. 29, 2007.

(51) Int. Cl.
G01N 33/574 (2006.01)

(52) U.S. Cl.
CPC ... *G01N 33/57449* (2013.01); *G01N 2800/50* (2013.01); *G01N 2800/52* (2013.01); *G01N 2800/60* (2013.01); *Y02A 90/22* (2018.01); *Y02A 90/26* (2018.01)

(58) Field of Classification Search
CPC .................................................. G01N 33/57449
See application file for complete search history.

(56) References Cited

U.S. PATENT DOCUMENTS

| | | |
|---|---|---|
| 3,935,562 A | 1/1976 | Stephens |
| 4,075,475 A | 2/1978 | Risby et al. |
| 4,122,343 A | 10/1978 | Risby et al. |
| 4,122,518 A | 10/1978 | Castleman et al. |
| 4,697,242 A | 9/1987 | Holland et al. |
| 4,881,178 A | 11/1989 | Holland et al. |
| 5,136,686 A | 8/1992 | Koza |
| 5,210,412 A | 5/1993 | Levis et al. |
| 5,352,613 A | 10/1994 | Tafas et al. |
| 5,553,616 A | 9/1996 | Ham et al. |
| 5,632,957 A | 5/1997 | Heller et al. |
| 5,649,030 A | 7/1997 | Normile et al. |
| 5,679,719 A | 10/1997 | Klemarczyk et al. |
| 5,687,716 A | 11/1997 | Kaufmann et al. |
| 5,697,369 A | 12/1997 | Long, Jr. et al. |
| 5,716,825 A | 2/1998 | Hancock et al. |
| 5,719,060 A | 2/1998 | Hutchens et al. |
| 5,769,074 A | 6/1998 | Barnhill et al. |
| 5,790,761 A | 8/1998 | Heseltine et al. |
| 5,825,488 A | 10/1998 | Kohl et al. |
| 5,839,438 A | 11/1998 | Graettinger et al. |
| 5,848,177 A | 12/1998 | Bauer et al. |
| 5,905,258 A | 5/1999 | Clemmer et al. |
| 5,946,640 A | 8/1999 | Goodacre et al. |
| 5,974,412 A | 10/1999 | Hazelhurst et al. |
| 5,989,824 A | 11/1999 | Birmingham et al. |
| 5,995,645 A | 11/1999 | Soenksen et al. |
| 6,007,996 A | 12/1999 | McNamara et al. |
| 6,025,128 A | 2/2000 | Veltri et al. |
| 6,035,230 A | 3/2000 | Kang et al. |
| 6,081,797 A | 6/2000 | Hitt |
| 6,114,114 A | 9/2000 | Seilhamer et al. |
| 6,128,608 A | 10/2000 | Barnhill |
| 6,157,921 A | 12/2000 | Barnhill |
| 6,225,047 B1 | 5/2001 | Hutchens et al. |
| 6,234,006 B1 | 5/2001 | Sunshine et al. |
| 6,248,063 B1 | 6/2001 | Barnhill et al. |
| 6,295,514 B1 | 9/2001 | Agrafiotis et al. |
| 6,311,163 B1 | 10/2001 | Sheehan et al. |
| 6,329,652 B1 | 12/2001 | Windig et al. |
| 6,427,141 B1 | 7/2002 | Barnhill |
| 6,493,637 B1 | 12/2002 | Steeg |
| 6,558,902 B1 | 5/2003 | Hillenkamp |
| 6,571,227 B1 | 5/2003 | Agrafiotis et al. |
| 6,615,199 B1 | 9/2003 | Bowman-Amuah |
| 6,631,333 B1 | 10/2003 | Lewis et al. |
| 6,675,104 B2 | 1/2004 | Paulse et al. |
| 6,680,203 B2 | 1/2004 | Drasseux et al. |
| 6,844,165 B2 | 1/2005 | Hutchens et al. |
| 6,925,389 B2 | 8/2005 | Hitt et al. |
| 7,027,933 B2 | 4/2006 | Paulse et al. |
| 7,057,168 B2 | 6/2006 | Miller et al. |
| 7,096,206 B2 | 8/2006 | Hitt |
| 7,240,038 B2 | 7/2007 | Hitt |
| 7,333,895 B2 | 2/2008 | Hitt et al. |
| 7,333,896 B2 | 2/2008 | Hitt et al. |
| 8,664,358 B2 | 3/2014 | Mansfield et al. |
| 9,274,118 B2 | 3/2016 | Mansfield et al. |

(Continued)

FOREIGN PATENT DOCUMENTS

| | | |
|---|---|---|
| GB | 2187035 | 8/1987 |
| WO | 1993/005478 | 3/1993 |

(Continued)

OTHER PUBLICATIONS

Office Action in corresponding Canadian Patent Application No. 2,691,980, dated Dec. 11, 2017 (3 pages).

(Continued)

*Primary Examiner* — Bin Shen
(74) *Attorney, Agent, or Firm* — Melissa Hunter-Ensor; Jana E. Harris; Greenberg Traurig, LLP

(57) ABSTRACT

Methods are provided for predicting the presence, subtype and stage of ovarian cancer, as well as for assessing the therapeutic efficacy of a cancer treatment and determining whether a subject potentially is developing cancer. Associated test kits, computer and analytical systems as well as software and diagnostic models are also provided.

18 Claims, No Drawings

(56) References Cited

U.S. PATENT DOCUMENTS

| | | |
|---|---|---|
| 2002/0059030 A1 | 5/2002 | Otworth et al. |
| 2002/0193950 A1 | 12/2002 | Gavin et al. |
| 2003/0054367 A1 | 3/2003 | Rich et al. |
| 2003/0077616 A1 | 4/2003 | Lomas |
| 2003/0129589 A1 | 7/2003 | Koster et al. |
| 2003/0134304 A1 | 7/2003 | van der Greef et al. |
| 2004/0053333 A1 | 3/2004 | Hitt et al. |
| 2004/0116797 A1 | 6/2004 | Takahashi et al. |
| 2004/0260478 A1 | 12/2004 | Schwamm |
| 2005/0059013 A1 | 3/2005 | Chan et al. |
| 2005/0069963 A1 | 3/2005 | Lokshin et al. |
| 2005/0209786 A1 | 9/2005 | Chen et al. |
| 2005/0214826 A1 | 9/2005 | Mor et al. |
| 2005/0260671 A1 | 11/2005 | Hitt |
| 2006/0064253 A1 | 3/2006 | Hitt et al. |
| 2006/0234287 A1 | 10/2006 | Erlander et al. |
| 2007/0003996 A1 | 1/2007 | Hitt et al. |
| 2007/0009543 A1 | 1/2007 | Burgess |
| 2007/0042405 A1 | 2/2007 | Lokshin |
| 2007/0185824 A1 | 8/2007 | Hitt |
| 2010/0055690 A1 | 3/2010 | Fung |
| 2010/0197561 A1 | 8/2010 | Fung |

FOREIGN PATENT DOCUMENTS

| | | |
|---|---|---|
| WO | 1994/001770 | 1/1994 |
| WO | 1997/049989 | 12/1997 |
| WO | 1999/041612 | 8/1999 |
| WO | 1999/047925 | 9/1999 |
| WO | 1999/058972 | 11/1999 |
| WO | 2000/049410 | 8/2000 |
| WO | 2000/055628 | 9/2000 |
| WO | 2001/020043 | 3/2001 |
| WO | 2001/031579 | 5/2001 |
| WO | 2001/031580 | 5/2001 |
| WO | 2001/084140 | 11/2001 |
| WO | 2002/006827 | 1/2002 |
| WO | 2002/059822 | 8/2002 |
| WO | 2002/061047 | 8/2002 |
| WO | 2002/088744 | 11/2002 |
| WO | 2003/031031 | 4/2003 |
| WO | 2003/062824 | 7/2003 |
| WO | 2004/103163 | 12/2004 |
| WO | 2006/006176 | 1/2006 |

OTHER PUBLICATIONS

English translation of Written Opinion for corresponding Brazilian Application No. PI0813002-7, dated Jul. 17, 2018 (9 pages).

Tong, C.S. et al., "Mass Spectral Search Method using the Neural Network Approach", International Joint Conference on Neural Networks, Washington, DC, Jul. 10-16, 1999, Proceedings, vol. 6 or 6, pp. 3962-3967.

Tsigkou, A. et al., "Total inhinin Is a Potential Serum Marker for Epithelial Ovarian Cancer", The Journal of Clinical Endocrinology and Metabolism, vol. 92, No. 7, Jul. 2007, pp. 2526-2531.

Tsukishiro, S. et al., "Preoperative serum thrombopoietin levels are highter in patients with ovarian cancer than with benign cysts", PubMed, Eur. J. Obstet Gynecol Reprod Biol., vol. 140, No. 1, Sep. 2008.

Van de Burg et al., "CA125 in ovarian cancer," The Netherlands Journal of Medicine, 40(1-2), pp. 36-51 (1992).

Veenstra, T.D. et al., "Multiple High-Resolution Serum Proteomic Patterns for Ovarian Cancer Detection", Proceedings of the American Association for Cancer Research, Jul. 2003, pp. 963-964, vol. 44, 2nd Edition.

Vlahou, A. et al., "Diagnosis of Ovarian Cancer Using Decision Tree Classification of Mass Spectral Data", Journal of Biomedicine and Biotechnology, vol. 5, 2003, pp. 308-314.

Von Eggeling, F. et al., "Mass Spectrometry Meets Chip Technology: A New Proteomic Tool in Cancer Research?", Electrophoresis, 2001, pp. 2898-2902, vol. 22, No. 14.

Voorhees, K.J., et al. "Approaches to Pyrolysis/Mass Spectrometry Data Analysis of Biological Materials," in Meuzelaar, H.L.C, Computer-Enhanced Analytical Spectroscopy, vol. 2, New York, Plenum Press, 1990, pp. 259-275.

Werther, W. et al., "Classification of Mass Spectra; a Comparison of Yes/No Classification methods for the Recognition of Simple Structural Properties", Chemometrics and Intelligent Laboratory Systems, 1994, pp. 63-76, vol. 22.

Wilding et al., "Application of Backpropogation Neutral Networks to Diagnosis of Breast and Ovarian Cancer," Cancer Letters, 1994, 77: 145-153.

Wilson, K. et al., "Expression of the Extracellular matrix protein tenascin in malidnant and benign ovarian tumours", British Journal of Cancer, vol. 74, 1996, pp. 999-1004.

Woong-Shick, A. et al. "Identification of hemoglobin-$\alpha$ and -$\beta$ subunits as potential serum biomarkers for the diagnosis and prognosis of ovarian cancer", Cancer Science, vol. 96, No. 3, Mar. 15, 2005, pp. 197-201.

Wu, B. et al., "Comparison of Statistical Methods for Classification of Ovarian Cancer Using Mass Spectrometry Data", Bioinformatics, 2003, pp. 1636-1643, vol. 19, No. 13.

Wu, S.P. et al., "SELDI-TOF MS Profiling of Plasma proteins in ovarian cancer", Taiwan Journal Obstet. Gynecol., vol. 15, No. 1, Mar. 2006.

Wythoff, B.J. et al., "Spectral Peak Verification and Recognition Using a Multilayered Neural Network", Analytical Chemistry, Dec. 15, 1990, pp. 2702-2709, vol. 62, No. 24.

Xiao, Z. et al., "Quantitation of Serum Prostate-Specific Membrane Antigen by a Novel Protein Biochip Immunoassay Discriminates Beign from Malignant Prostate Disease", Cancer Research, Aug. 15, 2001, pp. 6029-6033, vol. 61.

Xu, Y. et al., "Lysophosphatidic Acid as a Potential Biomarker for Ovarian and Other Gynecologic Cancers", Dreliminary Communication, JAMA, vol. 280, No. 8, Aug. 26, 1998, pp. 719-723.

Yao, X. et al., "Evolving Artificial Neural Networks for Medical Applications", Proceedings of the First Korea-Australia Joint Workshop on Evolutionary Computation, Sep. 1995, pp. 1-16.

Yates III, J.R., "Mass Spectrometry and the Age of the Proteome", Journal of Mass Spectrometry, 1998, pp. 1-19, vol. 33.

Ye, B., et al., "Proteomic-based discovery and characterization of glycosylated eosinophil-derived neurotoxin and COOH-terminal osteopontin fragments for ovarian cancer in urine" Clin Cancer Res, 2006. 12(2): p. 432-41.

Yu, J.S. et al., "Ovarian Cancer Identification Based on Dimensionality Reduction for High-Throughput Mass Spectrometry Data", Bioinformatics, 2005, pp. 2200-2209, vol. 21, No. 10.

Yurkovetsky, Z. et al., "Development of multimarker panel for early detection of endometrial cancer, High diagnostic power of prolactin", Gynecol Oncol., vol. 107, No. 1, Oct. 2007, pp. 58-65.

Yurkovetsky, Z. et al., Multiple biomarker panels for early detection of ovarian cancer, Future Oncology, Future Medicine Ltd., London, GB, vol. 2, No. 6, Dec. 1, 2006, pp. 733.741.

Zhang, J., Dynamics and Formation of Self-Organizing Maps: in Obermayer, H. et al. "Self-Organizing Map Formation: Foundations of Neural Computations", Oct. 2001, pp. 55-67.

Zhang, Z. et al., "Three Biomarkers Identified from Serum Proteomic Analysis for the Detection of Early Stage Ovarian Cancer", Cancer Research, vol. 64, Aug. 16, 2004, pp. 5882-5890.

Zhang, Z., "Combining Multiple Biomarkers in Clinical Diagnosis—A Review of Methods and Issues", Center for Biomarker Discovery, Department of Patholgy, Johns Hopkins Medical Institutions, 2001, 14 pages.

Zhao, C. et al., "Circulating Haptoglobin Is an Independent Prognosis Factor in the Sera of Patients with Epithelial Ovarian Cancer", Neoplasia, Brief Article, vol. 9, No. 1, Jan. 2007, pp. 1-7.

Moore, L. E., et al., "Evaluation of apoliprotein A1 and post-tranclationally modified forms of transthyretin as biomarkers for ovarian cancer detection in an independent study population", Cancer Epidemiol Biomarkers Prey, 2006. 15(9): p. 1641-6.

Mor, G. et al., "Serum protein markers for early detection of ovarian cancer," PNAS, vol. 102, No. 21, May 24, 2005, pp. 7677-7682.

(56) References Cited

OTHER PUBLICATIONS

Moscova et al., "Protein Chip Discovery of Secreted Proteins Regulated by the Phosphatidylinositol 3-Kinase Pathway in Ovarian Cancer Cell Lines", Cancer Research, vol. 66, Feb. 1, 2006, pp. 1376-1383.

Nakae, M., et al., "Preoperative [;as,a pstep[pmtom ;eve; as a nop,arler cp,[e,emtary to carbohydrate antigen 125 in predicting ovarian cancer", PubMed, J. Obstet Gynaecol Research, vol. 32, No. 3, Jun. 2006, 1 page.

Nikulin, A.E. et al., "Near-Optimal Region Selection for Feature Space Reduction: Novel Preprocessing Methods for Classifying MR Spectra", NMR Biomedicine, 1998, pp. 209-216, vol. 11.

Nilsson, T. et al., "Classification of Specied in the Genus *Penicillium* by Curie Point Pyrolysis/Mass Spectrometry Followed by Multivariate Analysis and Artificial Neural Networks", Journal of Mass Spectrometry, 1996, pp. 1422-1428, vol. 31.

Nozawa, et al., "Galactosyltransferase isozyme II (GT-II) as a new tumor marker for ovarian cancers—especially for clear cell carcinoma", Nihon Sanka Fujinka Gakkai Zasshi. Sep. 1989; vol. 41(9):1341-7.

Nozawa, S. et al., "Clinical significance of galactosyltransferase associate with tumor (GAT), a new tumor marker for Ovarian cancer—with special reference to the discrimincation between ovarian cancer and endometriosis", PubMed, Gan to Kagaku Ryoho., vol. 21, No. 4, Mar. 1994, pp. 507-516.

Office Action for European Patent Application No. 08781205.3, dated May 25, 2011, 9 pages.

Oh, J.M.C. et al., "A Database of Protein Expression in Lung Cancer", Proteomics, 2001, pp. 1303-1319, vol. 1.

Olah, T.V. et al., "The Simultaneous Determination of Mixtures of Drug Candidates by Liquid Chromatography/Atmospheric Pressure Chemical Ionization Mass Spectrometry as an In Vivo Drug Screening Procedure", Rapid Communications in Mass Spectrometry, 1997, pp. 17-23, vol. 11.

Paliouras, M., et al., "Human tisue kallikreins: the cancer biomarker family", PUbMed, Cancer Letter, vol. 249, No. 1, Apr. 28, 2007, 1 page.

Paulick, R. et al., "Clinical significance of different serum tumor markers in gynecological malignancies", PubMed, Sancer Detect Prevention, vol. 8, No. 1-2, 1985, 1 page.

Paweletz, C.P., "Rapid Protein Display Profiling of Cancer Progression Directly from Human Tissue Using a Protein Biochip", Drug Development Research, 2000, pp. 34-42, vol. 49.

PCT International Search Report and Written Opinion issued in International Application No. PCT/US08/68845 dated Nov. 24, 2008.

Pei, M. et al. "Feature Extraction Using Genetic Algorithms," Proceedings of the 1st International Symposium on Intelligent Data Engineering and Learning, IDEAL '98, Oct. 1998, pp. 371-384, Springer, Hong Kong.

Petricoin III, E.F. et al., "Clinical Applications of Proteomics", Journal of Nutrition, Jul. 2003, pp. 1-16, vol. 133, No. 7.

Petricoin III, E.F. et al., "Serum Proteomic Patterns for Detection of Prostate Cancer," Journal of National Cancer Institute, Oct. 16, 2002, pp. 1576-1578, vol. 94, No. 20.

Petricoin III, E.F. et al., "Use of Proteomic Patterns in Serum to Identify Ovarian Cancer", The Lancet, Feb. 16, 2002, pp. 572-577, vol. 359.

Pictet, O.V., et al., "Genetic Algorithms with Collective Sharing for Robust Optimization in Financial Applications", Olsen & Associates, Research Institute for Applied Econonomics, Jan. 22, 1996, pp 1-16.

Plebani, M. et al., "Combined use of urinary UGP and serum CA 125 in the diagnosis of gynecological cancers", PubMed, Anticancer Research, vol. 16, No. 6B, Nov.-Dec. 1996, 1 page.

Polanski, M. et al., "A List of Candidate Cancer Biomarkers for Targeted Proteomics", Original Research, Biomarker Insights, vol. 2, 2006, pp. 1-48.

Prior, C. et al., "Potential of Urinary Neopterin Excretion in Differentiating Chronic Non-A, Non-B Hepatitus from Fatty Liver", The Lancet, Nov. 28, 1987, pp. 1235-1237.

Purohit, P.V. et al., "Discriminant Models for High-Throughput Proteomics Mass Spectrometer Data", (Abstract), Proteomics—Clinical Adaptations, Sep. 9, 2003, pp. 1-2.

Reed, J., "Trends in Commerical Bioinformatics," Oscar Gruss Biotechnology Review, Mar. 2000, pp. 1-20.

Reibnegger, G. et al., "Neural Networks as a Tool for Utilizing Laboratiry Information: Comparison with Linear Discriminant Analysis with Classification and Regression Trees," Proceedings of the National Academy of Sciences, Dec. 1991, pp. 11426-11430, vol. 88.

Ricketts, I.W. et al., "Towards the Automated Prescreening of Cervical Smears", Mar. 11, 1992, Applications of Image Processing in Mass Health Screening, IEE Colloquium, pp. 1-4.

Roses, A.D., "Pharmacogenetics and the Practice of Medicine", Nature, Jun. 15, 2000, pp. 857-865, vol. 405.

Rosty, C. et al., "Identification of Hepatocarcinoma-Intesting-Pancreas/Pancreatic-Associated Protein I as a Biomarker for Pancreatic Ductal Adenocarcinoma by Protein Biochip Technology", Cancer Research, Mar. 15, 2002, pp. 1868-1875, vol. 62.

Roy, H.K., et al., "Biomarkers for the early detection of cancer: An inflammatory concept", Archives of Internal Medicine, American Medical Association, Chicago, IL, US, vol. 167, No. 17, pp. 1822, col. 2, paragraph 1, Sep. 24, 2007, pp. 1822-1824.

Rzymski, P. et al., "Evaluation of Serum SICAM-1 and CA-125 in patients with ovarian tumors—preliminary report", Ginekol. Pol., vol. 73, No. 11, Nov. 2002, 1 page.

Salford Systems, "Salford Systems White Paper Series," pp. 1-17 (online), retrieved on Oct. 17, 2000 from <URL: http://www/salford-systems.com/whitepaper.html>.

Sawada, M., et al., "Immunosuppresive acidic protein in patients with gynecologic cancer", PubMed, Cancer, vol. 54, No. 4, Aug. 15, 1984, 1 page.

Scambia, G., et al., "CA 15-3 as a tumor marker in gynecological malignancies", PubMed, Gynecological Oncology, vol. 30, No. 2, Jun. 1988.

Schmidt, H. et al., "Microfabricated Differenital Mobility Spectrometry with Pyrolysis Gas Chromatography for Chemical Characterization of Bacteria", Anal. Chem., 2004, pp. 5208-5217, vol. 76.

Scholler et al., "CA125 in ovarian cancer," Biomarkers in Medicine, 1(4), pp. 513-523, Dec. 2007.

Scholler, N. et al., "Bead-Based ELISA for Validation of Ovarian Cancer Early Detection Markers", Clinical Cancer Research, vol. 12, No. 7, Apr. 11, 2006, pp. 2117-2124.

Schroll, G. et al., "Applications of Artificial Intelligence for Chemical Inference, III. Aliphatic Ethers Diagnosed by Their Low-Resolution Mass Spectra and Nuclear Madnetic Resonance Data," Journal of the American Chemical Society, Dec. 17, 1969, pp. 7440-7445.

Schutyser, E. et al., "Identification of Biologically Active Chemokine Isoforms from Ascitic Fluid and Elevated Levels of CCL18/Pulmonary and Actication-regulated Chemokine in Ovarian Carcinoma", The Journal of Biological Chemistry, vol. 277, No. 27, Jul. 5, 2002, pp. 24584-25598.

Shaw, R.A. et al., "Infrared Spectroscopy of Exfoliated Cervical Cell Specimens," Analytical and Quantitative Cytology and Histology, Aug. 1999, pp. 292-302, vol. 21, No. 4.

Shevchenko, A. et al., "MALDI Quadupole Time-of-Flight Mass Spectrometry: A Powerful Tool for Proteomic Research", Analytical Chemistry, May 1, 2000, pp. 2132-2141, vol. 72, No. 9.

Shnayderman, M. et al., "Specied-Specific Bacteria Identification Using Differential Mobility Spectrometry and Bioinformatics Pattern Recognition", Anal. Chem., 2007, pp. 5930-5937, vol. 11.

Simon, I. et al. "B7-H4 is a Novel Membrane-Bound Protein and a Candidate Serum and Tissue Biomarker for Ovarian Cancer", Cancer Research, vol. 66, No. 3, Feb. 1, 2006, pp. 1570-1575.

Simon, R., "Development and Evaluation of Therapeutically Relevant Predictive Classifiers Using Gene Expression Profiling", Editorials, Journal of National Cancer Institute, vol. 98, No. 17, Sep. 6, 2006, pp. 1169-1171.

(56) References Cited

OTHER PUBLICATIONS

Skates, S. et al., "Pooling of Case Specimens to Create Standard Serum Sets for Screening Cancer Biomarkers", Cancer Epidemiol Biomarkers and Prevention, vol. 16, No. 2, Feb. 14, 2007, pp. 334-341.
Skates, S. et al., "Preoperative Sensitiveity and Specificity for Early-Stage Ovarian Cacner When Combining Cancer Antigen CA12511, CA 15-3, CA 72-4, and Macrophage Colony-Stimulating Factor Using Mixtures of Multivariate Normal Distributions", Journal of Clinical Oncology, Original Report, vol. 22, Bi, 20, Oct. 15, 2004, pp. 4059-4066.
Strouthopoulos, C. et al., "PLA Using RLSA and a Neural Network", Engineering Applications of Artificial Intelligence, 1999, pp. 119-138, vol. 12.
Sun, Z. et al., "A Protein Chip System for Parallel Analysis of Multi-Tumor Markers and its Application in Cancer Detection", Anticancer Research, vol. 24, 2004, pp. 1159-1166.
Taylor, J. et al., "The Deconvolution of Pyrolysis Mass Spectra Using Genetic Programming: Application to the Identification of Some *Eubacterium* Species," FEMS Microbiology Letters, 1998, pp. 237-246, vol. 160.
Tong, C.S. et al., "Mass Spectral Search Method using the Neural Network Approach", Chemometrics and Intelligent Laboratory Systems, 1999, pp. 135-150, vol. 49.
A. Ben-Aire, et al., "Elevated Serum Alkaline Phosphatase May Enable Early Diagnosis of Ovarian Cancer," PubMed, European Journal of Obstetrics and Gynecology Reproductive Biology, vol. 86, No. 1, Sep. 1999, 1 page.
A. Gaducci, et al., "The Serum Concentrations of TAG-72 Antigen Measured With CA 72-4 IRMA in Patients With Ovarian Carcinoma, Preliminary Data," PubMed, J. Nuci. med. Allied., Sci., vol. 33, No. 1, Jan.-Mar. 1989.
Adam, B.L. et al., "Serum Protein Fingerpriting Coupled with a Pattern Matching Algorithm Disctinguishes Prostate Cancer from Benign Prostate Hyperplasia and Healthy Men", Cancer Research, Jul. 1, 2002, pp. 3609-3614, vol. 62.
AE, Lokshin, et al., "Circulating IL-8 and Anti-IL-8 Autoantibody in Patients With Ovarian Cancer," PubMed, Gynecology Oncology, vol. 102, No. 2, Aug. 2006, 1 page.
Ahmed, N. et al., "Proteomic tracking of serum protein isoforms as screening biomarkers of ovarian cancer", PubMed, Proteomics, vol. 5, No. 17, Nov. 2005, 1 page.
Ahmed, Nuzhat, et al., "Cell-free 59 kDa Immunoreactive Integrin-Linked Kinase: A Novel Marker for Ovarian Carcinoma," Clinical Cancer Research, vol. 10, Apr. 8, 2004, pp. 2415-2420.
Ahmed, Nuzhat, et al., "Proteomic-based Identification of Haptoglobin-1 Precursor as a Novel Circulating Biomarker of Ovarian Cancer," British Journal of Cancer, vol. 91, 2004, pp. 129-140.
Al Mehta, et al., "Biomarker Amplification by Serum Carrier Protein Binding," PubMed, Dis Markers, vol. 19, No. 1, 2003-2004, 1 page.
Akçay, T. et al., "Significance of the 06-methylguanine-DNA methyltransferase and glutathione Stransferase activity in the era of patients with malignant and benign ovarian tumors", European Journal Obstet. Gynecol Reprod Biol., vol. 119, No. 1, Mar. 1, 2005, pp. 108-113.
Alaiya, A.A. et al., "Classification of Human Ovarian Tumors Using Multivariate Data Analysis of Polypeptide Expression Patterns", Int. J. Cancer, 2000, pp. 731-736, vol. 86.
An, Hyun, J., et al., "Profiling of Glycans in Serum for the Discovery of Potential Biomarkers for Ovarian Cancer," Journal of Proteome Research, American Chemical Society, vol. 5, 2006, pp. 1626-1635.
Ashfaq, R. et al., "Evaluation of PAPNET TM Systems for Rescreening of Negative Cervical Smears", Diagnostic Cytophathology, 1995, pp. 31-36, vol. 13, No. 1.
Astion, M.L. et al., "The Application of Backpropagation Neural Networks to Problems in Pathology and Laboratory Medicine", Arch. Pathol. Lab. Med, Oct. 1992, pp. 995-1001, vol. 116.
Atkinson, E.N. et al., "Statistical Tchniques for Diagnosing CIN Using Fluorescence Spectroscopy:SVD and CART", Journal of Cellular Biochemistry, 1995, Supplement 23, pp. 125-130.
Babaian, R.J. et al. "Performance of a Neural Network in Detecting Prostate Cancer in the Prostate-Specific Antigen Reflex Range of 2.5 to 4.0 ng/ml", Urology, 2000, pp. 1000-1006, vol. 56, No. 6.
Babcock, B. et al., "Ovarian and Breast Sytotoxic T Lymphocytes Can Recognize Peptides from the Amino Enhancer of Split Protein of the Notch Complex", Molecular Immunology, 1998, pp. 1121-1133, vol. 35.
Bailey-Kellogg, C. et al., "Reducing Mass Degeneracy in SAR by MS by Stable Isotopic Labeling," Journal of Computational Biology, 2001, pp. 19-36, vol. 8, No. 1.
Balteskard, L. et al., "Medical Diagnosis in the Internet age", The Lancet, Dec. 1999, siv 14, vol. 354.
Baron, A. T., et al., "Soluble epidermal growth factor receptor (sEGFR) [corrected] and cancer antigen 125 (CA125) as screening and diagnostic tests for epithelial ovarian cancer", Cancer Epidemiol Biomarkers Prey, 2005, 14(2): p. 306-18.
Baron-Hay, Sally, et al., "Elevated Serum Insulin-Like Growth Factor Binding Protein-2 as a Prognostic mMarker in Patients With Ovarian Cancer," Clinical Cancer Research, Mar. 10, 2004, pp. 1796-1806.
Bast Jr., R.C. et al., "Prevention and early detection of ovarian cancer: mission impossible?", PubMed, Recent Results Cancer Research, vol. 174, 2007, 1 page.
Bast, R.C., "Status of Tumor Markers in Ovarian Cancer Screening," Journal of Clinical Oncology, vol. 21, No. 105, May 15, 2003, pp. 200-205.
Belic, I. et al., "Neural Networks Methodologies for Mass Spectra Recognition", Vacuum, 1997, pp. 633-637, vol. 59, No. 7-9.
Belic, I., "Neural Networks Methodologies for Mass Spectra Recognition", 1995, pp. 375-380, additional details unknown.
Bellamy, J.E.C., "Medical Diagnosis, Diagnostic Spaces, and Fuzzy Systems", JAVMA, Feb. 1, 1997, pp. 390-396, vol. 210, No. 3.
Berikov, V.B. et al., "Regression Trees for Analysis of Mutational Spectra in Nucleotide Sequences", Bioimformatics, 1999, pp. 553-562, vol. 15, Nos. 7-8.
Bignotti, Eliana, et al., "Gene Expression Profile of Ovarian Serous Papillary Carcinomas: Identification of Metastasis-associated Genes," Research, Oncology, American Journal of Obstetrics & Gynecology, Mar. 2007, pp. 245.31-245e11.
Bittl, J.A., "From Confusion to Clarity: Direct Thrombin Inhibitors for Patients with Heparin-Induced Thrombocytopenia", Cath. and Cardio. Interventions, 2001, pp. 473-475, vol. 52.
Boran, N. et al., "Significance of serum and peritoneal fluid lactate dehydrogenase levels in ovarian cancer," PubMed, Gynecol Obstet Invest., vol. 49, No. 4, 2000, 1 page.
Breiman, L., et al., "Classification of Regression Trees" Boca Raton, Chapman & Hall/CRC, 1984, pp. 174-265 (Ch. 3, Medical Diagnosis and Prognosis).
Brown, M.P.S. et al., "Knowledge-Based Analysis of Microarray Gene Expression Data by Using Support Vector Machines", PNAS, Jan. 4, 2000, pp. 262-267, vol. 97, No. 1.
Cairns, A.Y. et al., "Towards the Automated Prescreening of Breast X-Rays", Alistair Gains, Department of Mathematics and Computer Science, University of Dundee, pp. 1-5.
Canadian Office Action for corresponding Canadian Application No. 2,691,980, dated Jan. 19, 2017 (5 pages).
Caprioli, R.M., et al., "Molecular Imagine of Biological Samples: Localization of Peptides and Proteins Using MALDI-TOF MS," Analytical Chemistry, 1997, pp. 4751-4760, vol. 69, No. 23.
Chace, D.H. et al., "Laboratory Integration and Utilization of Tandem Mass Spectrometry in Neonatal Screening: A Model for Clinical Mass Spectrometry in the Next Millennium", Acta Paediatr. Suppl. 432, 1999, pp. 45-47.
Chang, Et et al., "Using Genetic Algorithms to Select and Create Features for Pattern Classification", IJCNN International Joint Conference on Neural Networks, Jan. 8, 1991, pp. III-747 to III-752.
Chatterjee, Madhumita, et al., "Diagnostic Markers of Ovarian Cancer by High-Throughput Antigen Cloning and Detection on Arrays," Research Article, Cancer Research, Vo. 66, No. 2, Jan. 15, 2006, pp. 1181-1190.

(56) References Cited

OTHER PUBLICATIONS

Chen, et al., "Application of Serum Protein pattern model in diagnosis of colorectal cancer", Zhonghua Zhong Liu Za Zhi. Jul. 2004;26(7):417-20.

Chen, Yi-Ding, et al., "Artificial Neural Networks Analysis of Surface-Enhanced Laser Desorption/Ionization Mass Spectra Protein Pattern Distinguishes Colorectal Cancer From Healthy Population," Clinical Cancer Research, vol. 10, Dec. 15, 2004, pp. 8380-8385.

Christiaens, B. et al., "Fully Automated Method for the Liquid Chromatographic-Tandem Mass Spectrometric Determination of Cyproterone Acctate in Human Plasma Using Restricted Access Material for On-Line Sample Clean-Up", Journal of Chromatography A, 2004, pp. 105-110, vol. 1056.

Chu, et al., "Screening for Ovarian Cancer in the General Population," Billiere's Best Practice and Research Clinical Obstetrics and Gynecology Bailliere Tindall, London, vol. 20, No. 2 XP005329549, Apr. 1, 2006, pp. 307-320.

Chun, J. et al., "Long-term Identification of Streptomycetes Using Pyrolysis Mass Spectrometry and Artificial Neural Networks", Zbl. Nalt. 1997, pp. 258-266, vol. 285, No. 2.

Cicchetti, D.V., "Neural Networks and Diagnosis in the Clinical Laboratory: State of the Art", Clinical Chemistry, 1992, pp. 9-10, vol. 38, No. 1.

Ciphergen European Update, 2001, pp. 1-4, vol. 1.

CJ, Cox, et al., "Lacto-N-fucopentaose III Activity in the Serum of Patients With Ovarian Carcinoma," PubMed, Gynecology Obstetrics Invest, vol. 21, No. 3, 1986, 1 page.

Clarke, C. H., et al., Proteomics discovery of urinary biomarkers for early stage ovarian cancer, in 2007 Annual Meeting of AACR Conference. 2007: Los Angeles Convention Center, LA, Calif.

Claydon, M.A., et al., "The Rapid Idenitifcation of Intact Microorganisms Using Mass Spectrometry", Abstract, 1 page, online retrieved on Feb. 6, 2003 at <http://www.ncbi.nlm.nih.gov/entrz/query.fcgi?cmdfRetrieve&dh=PubMed&list_uids+963 . . . >.

Claydon, M.A., et al., "The Rapid Idenitifcation of Intact Microorganisms Using Mass Spectrometry", Nature Biotech, Nov. 1996, pp. 1584-1586, vol. 14.

Conrads, T.P. et al., "High-Resolution Serum Proteomic Features for Ovarian Cancer Detection", Endocrine-Related Cancer, 2004, pp. 163-178, vol. 11.

Crawford, L.R. et al., "Computer Methods in Analytical Mass Spectrometry; Empirical Identification of Molecular Class", Analytical Chemistry, Aug. 1968, pp. 1469-1474, vol. 40, No. 10.

CS, Diefenbach, et al., "Preoperative Serum YKL-40 is a Marker for Detection and Prognosis of Endometrial Cancer," PubMed, Gynecology Oncology, vol. 104, No. 2, Feb. 2007, 1 page.

Curry et al., "Msnet: A Neural Network that Classifies Mass Spectra", Standford University, Oct. 1990, Tetrahedron Computer Methodology, pp. 1-31.

DD, Taylor, et al., "Expression and Shedding of CD44 Variant Isoforms in Patients With Gynecologic Malignancies," PubMed, J. Soc. Gynecol. Investig., vol. 3, No. 5, Sep.-Oct. 1996, 1 page.

De Brabandere, V.I. et al., Isotope Dilution-Liquid Chromatography/Electrospray Ionization-Tandem Mass Spectrometry for the Determindation of Serum Thyroxine as a Potential Reference Method, Rapid Communications in Mass Spectrometry, 1998, pp. 1099-1103, vol. 12.

De Caceres, Inmaculada I., et al., "Tumor Cell-Specific BRCA1 and RASSFIA Hypermethylation in Serum Plasma, and Peritoneal Fluid for Ovarian Cancer Patients," Cancer Research, vol. 64, Sep. 16, 2004, pp. 6476-6481.

Devine, P.L. et al., "Serum mucin antigens CASA and MSA in tumors of the breast, ovary, lung, pancreas, bladder, colon, and prostate. A blind trial with 420 patients", PubMed, Cancer, vol. 72, No. 6, Sep. 15, 1993, 1 page.

Dhar, V. et al., "Seven Methods for Trasnforming Corporate Data Into Business Intelligence", Upper Saddle River, N.J., Prentice Hall, 1997, pp. 52-76.

Dhokia, B., et al., "A New Immunoassy Using Monoclonal Antibodies HMFG1 and HMFG2 Together With an Existing Marker CA125 for the Serological Detection and Management of Epithelial Ovarian Cancer," The Macmillian Press Ltd., Br, J. Cancer, vol. 54, 1986, pp. 891-895.

DM Robertson, et al., "Inhibin as a Diagnostic Marker for Ovarian Cancer," PubMed, Cancer Letter, vol. 249, No. 1, Apr. 28, 2007, 1 page.

Draghici, S. et al., "Epitomics: Serum screening for the early detection of cancer on microarrays using complex panels of tumor antigens", PubMed, Expert Rev Mol. Diagn., vol. 5, No. 5, Sep. 2005, 1 page.

Dudoit, S. et al. "Comparison of Discrimination Methods for the Classification of Tumors using Gene Expression Data", Mathematical Sciences Research institute, Berkeley, CA, Technical Report #576, Jun. 2000, pp. 1-43.

Dzeroski, S. et al., "Diterpene Structure Elucidation from 13C NMR-Spectra with Machine Learning", Boston, Kluwer Academic Publishers, Intelligent Data Analysis in Medicine and Pharmacology, 1997, pp. 207-225.

E. Miszczak-Zaborska, et al., "The Activity of Thymidine Phosphorylas as a New Ovarian Tumor Marker," PubMed, Gynecology Oncology, vol. 94, No. 1, Jul. 2004, 1 page.

Eghbaldar, A. et al. "Identification of Structural Features from Mass Spectrometry Using a Neural Network Approach: Application to Trimethylsilyl Derivatives Used for Medical Diagnosis", J. Chem. Inf. Comput. Sci., 1996, pp. 337-643, vol. 36, No. 4.

Einhorn, N., et al. "CA 125 assay used in conjunction with CA 15-3 and TAG-72 assays for discrimination between maliganant and non-malignant diseases of the ovary," PubMed, Ada Oncol., vol. 28, No. 5, 1989, 1 page.

Erkanli, Al, et al., "Application of Bayesian Modeling of Autologous Antibody Responses Against Ovarian Tumor-Associated Antigens to Cancer Detection," Research Article, Cancer Research, vol. 66, No. 3, Feb. 1, 2006, pp. 1792-1798.

Et, Fung, et al. "Classification of Cancer Types by Measuring Variants of Host Response Proteins Using SELDI Serum Assays," PubMed, Int. J. Cancer, vol. 115, No. 5, Jul. 2005, 1 page.

Extended Search Report Response for European Patent Application No. 08781205.3 filed on Mar. 30, 2011, 10 pages.

F. Kong, et al., "Using Proteomic Approaches to Identify new Biomarkers for Detection and Monitoring of Ovarian Sancer," PubMed, Gynecology Oncology, vol. 100, No. 2, Feb. 2006, 1 page.

F. Tas, et al., "The Value of Serum bcl-2 Levels in Advanced Epithelial Ovarian Cancer," PubMed, Oncol., vol. 23, No. 2, 2006, 1 page.

Fioretti, P. et al., "Preoperative evaluation of CA 125 and CA 19-9 serum levels in patients with ovarian masses," PubMed, Eur. J. Gynaecol. Oncol., vol. 9, No. 4, 1988, 1 page.

First Examination Report issued in Indian Patent Application No. 556/DELNP/2010 dated Nov. 4, 2016.

Freeman, R. et al., "Resolution of Batch Variations in Pyrolysis Mass Spectrometry of Bacteria by the Use of Artificial Neural Network Analysis", Antonie van Leeuwenhoek, 1995, pp. 253-260, vol. 8.

Furlong, J.W. et al., "Neural Network Analysis of Serial Cardiac Enzyme Data; A Clinical Application of Artificial Machine Intelligence," American Journal of Clinical Pathology, Jul. 1991, pp. 134-141, vol. 96, No. 1.

G. Scambia, et al., "Measurement of a Monoclonal-Antibody-defined Antigen (90K) in the Sera of Patients With Ovarian Cancer," PubMed, Anicancer Resarch, vol. 8, No. 4, Jul.-Aug. 1988, 1 page.

Gaskell, S.J., "Electrospray: Principles and Practice", Journal of Mass Spectrometry, 1997, pp. 677-688, vol. 32.

GB, Massi, et al., "The Significance of Measurement of Several Ocofetal Antigens in Diagnosis and Management of Epithelial Ovarian Tumors," PubMed, European Journal of Gynecology Oncology, vol. 4, No. 2, 1983, 1 page.

George, S.E., "A Visualization and Design Tool (AVID) for Data Mining with the Self-Organizing Feature Map", International Journal on Artificial Intelligence Tools, 2000, pp. 369-375, vol. 9, No. 3.

(56) References Cited

OTHER PUBLICATIONS

Gerhardt, Willie, et al., "Troponin T: A Sensitive and Specific Diagnostic and prognostic Marker of Myocardial Damage," Clinica Chimica Acta, vol. 272, 1998, pp. 47-57.
Golub, T.R. et al., "Molecular Classification of Cancer: Class Discovery and Class Prediction by Gene Expression Monitoring", Science, Oct. 15, 1999, pp. 531-537, vol. 286.
Goodacre et al., "Correction of Mass Spectral Drift using Artificial Neural Networks", Analytical Chemistry, 1996, pp. 271-280, vol. 68.
Goodacre, R. et al., "Discrimination between Methicillin-Resistant and Methicillin-Susceptible *Staphylococcus aureus* Using Pyrolysis Mass Spectrometry and Artificial Neural Networks", Journal of Antimicrobal Chemotherapy, 1998, pp. 27-34, vol. 41.
Goodacre, R. et al., "Identification and Discrimiation of Oral Asaccharolytic *Eubacterium* spp. by Pyrolysis Mass Spectrometry and Artificial Neural Networks", Current Microbiology, 1996, pp. 77-84, vol. 32.
Goodacre, R. et al., "Quantitative Analysis of Multivariate Data Using Artificial Neural Networks: A Tutorial Review and Applications to the Deconvolution of Pyrolysis Mass Spectra", Zbl. Bakt. 1996. pp. 516-539, vol. 284.
Goodacre, R. et al., "Rapid Identification of Urinary Tract Infection Bacteria Using Hyperspectral Whole-Organism Fingerprinting and Artificial Neural Networks", Microbiology, 1998, pp. 1157-1170, vol. 144.
Goodacre, R. et al., "Sub-Species Discrimination, Using Pyrolysis Mass Spectrometry and Self-Organising Neural Networks, of Propionibacterium acnes Isolated from Normal Human Skin", Zbl. Bakt., 1996, pp. 501-515, vol. 284.
Gorelik, Elieser, et al., "Multiplexed Immunobead-Based Cytokine Profiling for Early Detection of Ovarian Cancer," Short Communication, Cancer Epidemiology, Biomarkers & Prevention, vol. 14, No. 4, Apr. 2005, pp. 981-987.
Gray, N.A.B., "Constraints on 'Learning Machine' Classidication Methods," Analytical Chemistry, Dec. 1976, pp. 2265-2268, vol. 48, No. 14.
H. Kobayashi, et al., "Clinical Evaluation of Circulating Serum Sialyl Tn Antigen Levels in Patients With Epithelial Ovarian Cancer," PubMed, J. Clin. Oncol., vol. 9, No. 6, Jun. 1991, 1 page.
H. Koebl, et al., "A Comparative Study of Immunosuppressive Acidic Protein (IAP), CA 125 and Acute-Phase Proteins as Parameters for Ovarian Cancer Monitoring," Neoplasma, Vydavatel'stvo slovenskej, Akademie Vied Veda, SK, vol. 35, No. 2, XP009011458, Jan. 1, 1988, pp. 215-220.
H. Meden, et al., "Elevated Serum levels of a C-erB-2 Oncogene Product in Ovarian Cancer Patients and in Pregnancy," PubMed, J. Cancer Res. Clin. Oncol., vol. 120, No. 6, 1994, 1 page.
H. Yabushita, et al., "Combination Assay of CA 125, TPA, IAP, CEA, and Ferritin in Serum for Ovarian Cancer," JubMed, Gynecol. Oncol., vol. 29, No. 1, Jan. 1988, 1 page.
H. Zhang, et al., "Biomarker Discovery for Ovarian Cancer Using SELDI-TOF-MS," PubMed, Gynecol. Oncol., vol. 102, No. 1, Jul. 2005, 2 pages.
Hackett, P.S. et al., "Rapid SELDI Biomarker Protein Profiling of Serum from Normal and Prostate Cancer Patients", American Association for Cancer Research (abstract only), Mar. 2000, pp. 563-564, vol. 41.
Halket, J.M., et al., "Deconvolution Gas Chromatography/Mass Spectrometry of Urinary Organic Acids—Potential for Pattern Recognition and Automated Identification of Metabolic Disorders", Rapid Communications in Mass Spectrometry, 1999, pp. 279-284, vol. 13.
Hashemi, R.R. et al., "Identifying and Testing of Signatures for Non-Volatile Biomolecules Using Tandem Mass Spectra", SIGBIO Newsletter, Dec. 1995, pp. 11-19, vol. 15, No. 3.
Hausen, A. et al. "Determination of Neopterine in Human Urine by Reversed-Phase High-Performance Liquid Shromatography", Journal of Chromatography, 1982, pp. 61-70, vol. 227.

Helfer, L.A., et al., "Serum C-reactive Protein as Independent Prognostic Variable in Patients With Ovarian Cancer," Clinical Cancer Research, The American Association for Cancer Research US Lnkddoi, vol. 14, No. 3, Feb. 1, 2008, pp. 710-714.
Hellstrom Ingegerd, et al., "Mesothelin Variant 1 Is Released From Tumor Cells as a Diagnostic Marker," Cancer Epidemiology Biomarkers & Prevention, vol. 15, No. 5, May 15, 2006, pp. 1015-1020.
Hess, K.R. et al., "Classification and Regression Tree Analysis of 1000 Consecutive Patients with Unknown Primary Carcinoma", Clinical Cancer Research, Nov. 1999, pp. 3403-3410, vol. 5.
Holland, J.H., "Adaption in Natural and Artificial Systems: An Introductory Analysis with Applications to Biology, Control, and Artificial Intelligence", 2001, pp. 1-31; 89-120, MIT Press.
HR 3rd, Bergen, et al., "Discovery of Ovarian Cancer Biomarkers in Serum Using NanoLC Electrospray Ionization TOF and FT-ICR mass Spectrometry," PubMed, Dis Markers, vol. 19, No. 4-5, 2003-2004, 1 page.
I. Simon, et al. "Evaluation of the Novel Serum Markers B7-H4, Spondin 2, and DCR3 for Diagnosis and Early Detection of Ovarian Cancer," PubMed, Gynecology Oncology, vol. 106, No. 1, Jul. 2007, 1 page.
Inoue, et al., "The clinical value of sialyl SSEA-1 antigen in patients with gynecologic tumors", Nihon Sanka Fujinka Gakkai Zasshi. Dec. 1987;39(12):2120-4.
International Search Report and Written Opinion from International Application No. PCT/US08/68845, dated Nov. 24, 2008, 6 pages.
J. Tosner, et al, "Serum Prealbumin, Transferrin and Alpha-1 Acid Glycoprotein in Patients with Gynecological Carcinomas," PubMed, Neoplasma, vol. 35, No. 4, 1988, 1 page.
Jain, A.K. et al., "Statistical Pattern Recognition: A Review", IEEE Transactions on Pattern Analysis and Machine Intelligence, Jan. 2000, pp. 4-37, vol. 22, No. 1.
Jellum, E. et al., "Mass Spectrometry in Diagnosis of Metabolic Disorders", Biomedical and Environmental Mass Spectrometry, 1988, pp. 57-62, vol. 16.
Jie-Kai, Yu, et al., "An Integrated Approach Utilizing Proteomics and Bioinformatics to Detect Ovarian Cancer," Journal of Zhejiang University Science, vol. 6B, No. 4, 2005, pp. 227-231.
Jurs, P.C. et al., "Computerized Learning Machines Appled to Chemical Problems; Molecular Formula Determination from Low Resolution Mass Spectrometry", Analytical Chemistry, Jan. 1969, pp. 21-27, vol. 41, No. 1.
Kenyon, R.G.W. et al., "Application of Neural Networks to the Analysis of Pyrolysis Mass Spectra", Zbl. Bakt., 1997, pp. 267-277, vol. 285.
Kiem, H. et al., "Using Rough Genetic and Kohonen's Neural Network for Conceptual Cluster Discovery in Data Mining", New Directions in Rough Sets, Data Mining and Granular-Soft Computing, International Workshop, RSFDGRC, Nov. 9, 1999, pp. 448-452.
Kizawa et al., Diagnostics value of biochemical tumor markers in serum of patients with cancer of the ovary, PubMed, Nihon Sanka Fujinka Gakkai Zasshi, vol. 35, No. 3, 1983, pp. 251-258.
Knauf, S. et al., "A Study of the NB/70K and CA 125 monoclonal antibody radioimmunoassays for measuring serum antigen levels in ovarian cancer patients", PubMed, Am. J. Obstet Gynecol., vol. 152, No. 7, Pt. 1, Aug. 1985, 1 page.
Koelbl H et al "A Comparative Study of Mucin-like Carcinoma-Associated Antigen (MCA), CA 125, CA 19-9 and SEA in Patients With Ovarian Cancer," PubMed, Neoplasma, vol. 36, No. 4, 1989, 1 page.
Koelbl, H., et al., "Vergleichende Untersuchungen Ueber Die Wertigkeit Von Akute-Phase Proteinen Und Ca-125 Fuer Das Monitoring Von Patientinnen Mit Ovarialkazinomiicomparative Study for the Value of Acute-PhaseProteins and Ca-125 in the Monitoring of Patients With Maligna," Strahientherapie Und Onkologie, Urban Und Vogel, Muenchen, DE, vol. 164, No. 12, XP008056603, ISSN,: 0179-7158, abstract, p. 725, col. 2, paragraph 2, figures 1,2; table 2, p. 727, col. 2, paragraphs 2,3, Jan. 1, 1988, pp. 724-728.
Kohavi, R. et al., "Wrappers for Feature Subset Selection", Artificial Intelligence, 1997, pp. 273-324, vol. 97.

(56) References Cited

OTHER PUBLICATIONS

Kohno, H. et al., "Quantitative Analysis of Scintiscan Matrices by Computer," Japanese Journal of Medical Electronics and Biological Engineering, Aug. 1974, pp. 22-29, English Abstract.

Kohonen, T., "Self-Organization and Associative Memory", Springer 1988, pp. 30-67.

Kohonen, T., "Self-Organizing Maps", Springer 2001, pp. 1-70.

Koivunen, Erkki, et al., "Identification of Biomarkers for Ovarian Cancer Using Strong Anion-Exchange Protein Chips: Potential Use in Diagnosis and Prognosis," PNAS, vol. 100, No. 21, Oct. 14, 2003, pp. 12343-12348.

KR, Kozak, et al., "Characterization of Serum Biomarkers for Detection of Early Stage Ovarian Cancer," PubMed, Proteomic,s, vol. 5, No. 17, Nov. 2005, 1 page.

Krishnamurthy, T. et al., "Detection of Pathogenic and Non-Pathogenic Bacteria by Matrix-Assisted Laster Desorption Ionization Time-of-Flight Mass Spectrometry", Rapid Comms. in Mass Spectrometry, 1996, pp. 883-888, vol. 10.

Kwata, H. et al., "The Survival of Ingested Lacroferrin in the Gastrointestinal Tract of Adult Mice", Biochem. J., 1998, pp. 321-323, vol. 334.

Lambeck, Annechien J., et al., "Serum Cytokine Profiling as a Diagnostic and Prognostic Tool in Ovarian Cancer: A Potential Role for Interleukin 7," Clinical Cancer Research, vol. 13, No. 8, Apr. 16, 2007, pp. 2385-2391.

Langdon, W.B., "Natural Language Text Classification and Filtering with Trigrams and Evolutionary Nearest Neighbour Classifiers", CWI Report, Jul. 31, 2000, pp. 1-12.

LePage, Cecile, et al., "From Gene Profiling to Diagnostic Markers: IL-18 and FGF-2 Complement CA125 as Serum-based Markers in Epithelial Ovarian Cancer," PubMed, Int. J. Cancer, vol. 118, No. 7, Apr. 1, 2006, pp. 1750-1758.

Lewis, R.J., "An Introduction to Classification and Regression Tree (CART) Analysis", presented at 2000 Annual Meeting of the Society for Academic Emergency Medicine in San Franscisco, CA, 2000, pp. 1-14.

Li, J. et al. "Proteomics and Bioinformatics Approaches for Identification of Serum Biomarkers to Detect Breast Cancer", Clinical Chemistry, 2002, pp. 1296-1304, vol. 48, No. 8.

Lim, R. et al., "Neutrophil gelatinase-associated lipocalin (NGAL) an early-screening biomarker for ovarian cancer L NGAL is associated with epidermal growth factor-induced epitheliomesenchymal transition", PubMed, Int. J. Cancer, vol. 120, No. 11, Jun. 1, 2007, 1 page.

Lin, Y.W., et al., "Plasma proteomic patterns as biomarkers for ovarian cancer", International Journal of Gynecol. Cancer, vol. 16, Supplemental 1, Jan.-Feb. 2006, pp. 139-146.

Liotta, L. et al., "Molecular Profiling of Human Cancer", Nature Genetics, Oct. 2000, pp. 827-836, vol. 405.

Lockhardt et al., "Genomics, Gene Expression and DNA Arrays", Nature, Jun. 2000, pp. 827-836, vol. 405.

Loging, T.W. et al., "Identifying Potential Tumor Markers and Antigens by Database Mining and Rapid Expression Screening", Genome Research, Sep. 2000, pp. 1393-1402, vol. 10, No. 9.

Lokshin, Anna E., et al., "Multipiexed Biomarkers for Early Detection of Ovarian Cancer," Proceedings of the Annual Meeting of the American Association for Cancer Research 96th Annual Meeting of the American Association for Cancer Research, vol. 46, Apr. 1, 2005, p. 379.

Lopez M. F., et al., "A novel, high-throughput workflow for discovery and identification of serum carrier protein-bound Peptide biomarker candidates in ovarian cancer samples", Clin Chem, 2007. 53(6): p. 1067-74.

Lowry, S.R. et al., "Comparison of Various K-Nearest Neighbor Voting Schemes with the Self-Training Interpretive and Retrieval System for Identifying Molecular Substructures for Mass Spectral Data", Analytical Chemistry, Oct. 1977, pp. 1720-1722, vol. 49, No. 12.

Lundqvist, E.A., et al., "Evaluation of Seven Different Tumor Markers for the Establishment of Tumor Marker Panels in Gynecologic Maligancies," European Journal of Gyynacological, Oncology, Sermes, Padova, IT, vol. 10, No. 6, XP008125704, p. 397, col. 1, paragraph 2, p. 401, col. 1, paragraph 5-col. 2, paragraph 1, p. 404, .1olumn 1, paragraph 1-col. 2, paragraph 1-3, Jan. 1, 1989, pp. 395-405.

Luo, Y. et al., Quantification and Confirmation of Flunixin in Equine Plasma by Liquid Chromatograph—Quadrupole Time-Of-Flight Tandem Mass Spetrometry, Journal of Chromatography B, 2004, pp. 173-184, vol. 801.

M. Inoque, et al., "Sialyl Lewis-Xi Antigen in Patients With Gynecologic Tumors," PubMed, Obstet Gynecol, vol. 73, No. 1, Jan. 1989, 1 page.

MacFie, H.J.H. et al., "Use of Canonical Variates Analysis in Differentiation of Bacteria by Pyrolysis Gas-Liquid Chromatography", Journal of General Microbiology, 1978, pp. 67-74, vol. 104.

Malins, D.C. et al., "Models of DNA Structure Achieve Almost Perfect Discrimination Between Normal Prostate, Beign Prostatic Hyperplasia (BPH), and Adenocarcinoma and Have a High Potential for Predicting BPH and Prostrate Cancer", Proceedings of the National Academy of Sciences, Jan. 1997, pp. 259-264, vol. 94.

Malki, S., et al., "Expression and biological role of the prostaglandid D synthase/SOX9 pathway in human ovarian Cancer cells", PubMed, Cancer Letter, vol. 255, No. 2, Oct. 8, 2007, 1 page.

Marvin, L.F. et al., "Characterization of a Novel Speial Officinalis Neuropeptide using MALDI-TOL MS and Post-Source Secay Analysis", Peptides, 2001, pp. 1391-1396, vol. 22.

McSorley, M., et al., "C-reactive protein concentrations and subsequent ovarian cancer risk", Obstetrics and Gynecology, Lippincott Williams & Wilkins, vol. 109, No. 4, Apr. 1, 2007, pp. 933-941.

Meinhold-Heerlein, I. et al., "An Integrated Clinical-Genomics Approach Identifies a Candidate Multi-Analyte Blood Test for Serious Ovarian Carcinoma", Clinical Cancer Research, vol. 13, No. 2, Jan. 25, 2007, pp. 458-466.

Meuzelaar, H.L.C. et al., "A Technique for Fast and Reproducible Fingerprinting of Bacteria by Pyrolysis Mass Spectrometry", Analytical Chemistry, Mar. 1973, pp. 587-590, vol. 45, No. 3.

Meyer, B. et al., "Identifications of the 1H-NMR Spectra of Complex Oligosaccharides with Artificial Neural Networks", Science, Feb. 1991, pp. 542-544, vol. 251.

Microsoft Press Computer Dictionary, Second Edition, The Comprehensive Standard for Business, School, Library, and Home, Microsoft Press Redmond, WA, 1994, pp. 87 and 408.

Moler, E.J. et al., "Analysis of Molecular Profile Data Using Generative and Discriminative Methods", Physiol. Genomics, Dec. 2000, pp. 109-126, vol. 4.

Hellstrom et al., "The HE4 (WFDC2) protein is a biomarker for ovarian carcinoma," Cancer Research, 2003; vol. 63, No. 13, pp. 3695-3700.

Holmquist et al., "Quantification of human serum apolipoprotein A-I by zone immunoelectrophoresis assay and a procedure for the preparation of an A-I standard," Clinica Chimica Acta, 1986; vol. 156, No. 2, pp. 131-143.

Monnet et al., "Clinical value of C-reactive protein, alpha 1-glycoprotein acid and transferrin assay in homozygous sickle cell disease," Bulletin de la Societe de pathologie exotique (1990), 1993; vol. 86, No. 4, pp. 282-285 (English Abstract).

Reichert et al., "Application of a tissue receptor assay to measurement of serum follitropin (FSH)," The Journal of Clinical Endocrinology and Metabolism, 1975; vol. 41, No. 3, pp. 634-637.

Office Action in corresponding Canadian Patent Application No. 2,691,980, dated Nov. 26, 2019 (5 pages).

PREDICTIVE BIOMARKERS FOR OVARIAN CANCER

CROSS REFERENCE TO RELATED APPLICATIONS

This application is a continuation of U.S. patent application Ser. No. 15/041,754, filed on Feb. 11, 2016, which is now U.S. Pat. No. 9,846,158, issued on Dec. 19, 2017, which is a continuation of U.S. patent application Ser. No. 14/172,237, filed on Feb. 4, 2014, which is now U.S. Pat. No. 9,274,118, issued on Mar. 1, 2016, which is a divisional of U.S. patent application Ser. No. 12/165,240, filed on Jun. 30, 2008, which is now U.S. Pat. No. 8,664,358, issued on Mar. 4, 2014, which claims priority under 35 USC Section 119 to Provisional Patent Applications Serial Nos. 60/947,253, filed on Jun. 29, 2007, and 61/037,946, filed on Mar. 19, 2008, the disclosures of which are hereby incorporated by reference in their entireties.

FIELD OF THE INVENTION

This invention provides methods for predicting and diagnosing ovarian cancer, particularly epithelial ovarian cancer, and it further provides associated analytical reagents, diagnostic models, test kits and clinical reports.

BACKGROUND

The American Cancer Society estimates that ovarian cancer will strike 22,430 women and take the lives of 15,280 women in 2007 in the United States. Ovarian cancer is not a single disease, however, and there are actually more than 30 types and subtypes of ovarian malignancies, each with its own pathology and clinical behavior. Most experts therefore group ovarian cancers within three major categories, according to the kind of cells from which they were formed: epithelial tumors arise from cells that line or cover the ovaries; germ cell tumors originate from cells that are destined to form eggs within the ovaries; and sex cord-stromal cell tumors begin in the connective cells that hold the ovaries together and produce female hormones.

Common epithelial tumors begin in the surface epithelium of the ovaries and account for about 90 percent of all ovarian cancers in the U.S. (and the following percentages reflect U.S. prevalence of these cancers). They are further divided into a number of subtypes—including serous, endometrioid, mucinous, and clear cell tumors—that can be further subclassified as benign or malignant tumors. Serous tumors are the most widespread forms of ovarian cancer. They account for 40 percent of common epithelial tumors. About 50 percent of these serous tumors are malignant, 33 percent are benign, and 17 percent are of borderline malignancy. Serous tumors occur most often in women who are between 40 and 60 years of age.

Endometrioid tumors represent approximately 20 percent of common epithelial tumors. In about 20 percent of individuals, these cancers are associated with endometrial carcinoma (cancer of the womb lining). In 5 percent of cases, they also are linked with endometriosis, an abnormal occurrence of endometrium (womb lining tissue) within the pelvic cavity. The majority (about 80 percent) of these tumors are malignant, and the remainder (roughly 20 percent) usually is borderline malignancies. Endometrioid tumors occur primarily in women who are between 50 and 70 years of age.

Clear cell tumors account for about 6 percent of common epithelial tumors. Nearly all of these tumors are malignant. Approximately one-half of all clear cell tumors are associated with endometriosis. Most patients with clear cell tumors are between 40 and 80 years of age.

Mucinous tumors make up about 1 percent of all common epithelial tumors. Most (approximately 80 percent) of these tumors are benign, 15 percent are of borderline malignancy, and only 5 percent are malignant. Mucinous tumors appear most often in women between 30 to 50 years of age.

Ovarian cancer is by far the most deadly of gynecologic cancers, accounting for more than 55 percent of all gynecologic cancer deaths. But ovarian cancer is also among the most treatable—if it is caught early. When ovarian cancer is caught early and appropriately treated, the 5-year survival rate is 93 percent. See, for example, Luce et al, "Early Diagnosis Key to Epithelial Ovarian Cancer Detection," The Nurse Practitioner, December 2003 at p. 41. Extensive background information about ovarian cancer is readily available on the internet, for example, from the "Overview: Ovarian Cancer" of the Cancer Reference Information provided by the American Cancer Society (www.cancer.org) and the NCCN Clinical Practice Guidelines in Oncology™ Ovarian Cancer V.1.2007 (www.nccn.org).

The current reality for the diagnosis of ovarian cancer is that most cases—81 percent of all cases of ovarian cancer—are not caught in earliest stage. This is because early stage ovarian cancer is very difficult to diagnose. Its symptoms may not appear or be noticed at this point. Or, symptoms—such as bloating, indigestion, diarrhea, constipation and others—may be vague and associated with many common and less serious conditions. Most importantly, there has been no effective test for early detection. An effective tool for early and accurate detection of ovarian cancer is a critical unmet medical need.

Biomarkers for Ovarian Cancer

A variety of biomarkers to diagnose ovarian cancer have been proposed, and elucidated through a variety of technology platforms and data analysis tools. An interesting compilation of 1,261 potential protein biomarkers for various pathologies was presented by N. Leigh Anderson et al., "A Target List of Candidate Biomarkers for Targeted Proteomics," Biomarker Insights 2:1-48 (2006). A spreadsheet listing the markers discussed in this paper can be found at the website of the Plasma Proteome Institute (www.plasmaproteome.org). Several published studies are described immediately below and a number of other studies are listed as references at the end of this specification. All of these studies, all other documents cited in this specification, and related provisional patent application Ser. Nos. 60/947,253 filed Jun. 29, 2007 and 61/037,946 filed Mar. 19, 2008, are hereby incorporated by reference in their entireties.

For example, Cole, "Methods for detecting the onset, progression and regression of gynecologic cancers." U.S. Pat. No. 5,356,817 (Oct. 18, 1994) described a method for detecting the presence of a gynecologic cancer in a female, said cancer selected from the group consisting of cervical cancer, ovarian cancer, endometrial cancer, uterine cancer and vulva cancer, the method comprising the steps of: (a) assaying a plasma or tissue sample from the patient for the presence of CA 125, and at or about the same time; and (b) assaying a bodily non-blood sample from said patient for the presence of human chorionic gonadotropin beta-subunit core fragment, wherein the detection of both CA 125 and human chorionic gonadotropin beta-subunit core fragment is an indication of the presence of a gynecological cancer in the female. A measurement of the human chorionic gonadotropin beta-subunit core fragment alone was stated to be useful in monitoring progression and regression of such cancers.

Fung et al, "Biomarker for ovarian and endometrial cancer: hepcidin," U. S. Patent Application 20070054329, published Mar. 8, 2007, describes a method for qualifying ovarian and endometrial cancer status based on measuring hepcidin as a single biomarker, and based on panels of markers including hepcidin plus transthyretin, and those two markers plus at least one biomarker selected from the group consisting of: Apo A1, transferrin, CTAP-III and ITIH4 fragment. An additional panel further includes beta-2 microglobulin. These biomarkers were measured by mass spectrometry, particularly SELDI-MS or by immunoassay. And data was analyzed by ROC curve analysis.

Fung et al. also described the use of hepcidin levels used in combination with other biomarkers, and concluded that the predictive power of the test was improved. More specifically, increased levels of hepcidin together with decreased levels transthyretin were correlated with ovarian cancer. Increased levels of hepcidin together with decreased levels of transthyretin, together with levels of one or more of Apo A 1 (decreased level), transferrin (decreased level), CTAP-III (elevated level) and an internal fragment of ITIH4 (elevated level) were also correlated with ovarian cancer. The foregoing biomarkers were to further be combined with beta-2 microglobulin (elevated level), CA125 (elevated level) and/or other known ovarian cancer biomarkers for use in the disclosed diagnostic test. And hepcidin was said to be hepcidin-25, transthyretin was said to be cysteinylated transthyretin, and/or ITIH4 fragment perhaps being the ITIH4 fragment 1.

Diamandis, "Multiple marker assay for detection of ovarian cancer," U. S. Patent Application 20060134120 published Jun. 22, 2006, described a method for detecting a plurality of kallikrein markers associated with ovarian cancer and optionally CA125, wherein the kallikrein markers comprise or are selected from the group consisting of kallikrein 5, kallikrein 6, kallikrein 7, kallikrein 8, kallikrein 10, and kallikrein 11. His patent application explained that a significant difference in levels of these kallikreins, which are a subgroup of secreted serine proteases markers, and optionally that also of CA125, relative to the corresponding normal levels, was indicative of ovarian cancer. By repeatedly sampling these markers in the same patient over time, Diamandis also found that a significant difference between the levels of the kallikrein markers, and optionally CA125, in a later sample, relative to an earlier sample, is an indication that a patient's therapy is efficacious for inhibiting ovarian cancer. Samples were evaluated by protein binding techniques, for example, immunoassays, and by nucleotide array, PCR and the like techniques.

Gorelik et al, Multiplexed Immunobead-Based Cytokine Profiling for Early Detection of Ovarian Cancer" in Cancer Epidemiol Biomarkers Prev. 2005:14(4) 981-7 (April 2005) reported that a panel of multiple cytokines that separately may not show strong correlation with the disease provide diagnostic potential. A related patent application appears to be Lokshin et al., "Multifactorial assay for cancer detection," U. S. Patent Application 20050069963 published Mar. 31, 2005. According to the journal article, a novel multianalyte LabMAP profiling technology was employed that allowed simultaneous measurement of multiple markers. Various concentrations of 24 cytokines (cytokines/chemokines, growth, and angiogenic factors) in combination with CA-125 were measured in the blood sera of 44 patients with early-stage ovarian cancer, 45 healthy women, and 37 patients with benign pelvic tumors.

Of the cytokines discussed by Gorelik et al., six markers, specifically interleukin (IL)-6, IL-8, epidermal growth factor (EGF), vascular endothelial growth factor (VEGF), monocyte chemoattractant protein-1 (MCP-1), together with CA-125, showed significant differences in serum concentrations between ovarian cancer and control groups. Out of those markers, IL-6, IL-8, VEGF, EGF, and CA-125, were used in a classification tree analysis that reportedly resulted in 84% sensitivity at 95% specificity. The receiver operator characteristic curve (ROC) described using the combination of markers produced sensitivities between 90% and 100% and specificities of 80% to 90%. Interestingly, the receiver operator characteristic curve for CA-125 alone resulted in sensitivities of 70% to 80%. The classification tree analysis described in the paper for discrimination of benign condition from ovarian cancer used CA-125, granulocyte colony-stimulating factor (G-CSF), IL-6, EGF, and VEGF which resulted in 86.5% sensitivity and 93.0% specificity. The authors concluded that simultaneous testing of a panel of serum cytokines and CA-125 using LabMAP technology presented a promising approach for ovarian cancer detection.

A related patent application by Lokshin, "Enhanced diagnostic multimarker serological profiling," U. S. Patent Application 20070042405 published Feb. 22, 2007 describes various biomarker panels and associated methods for diagnosis of ovarian cancer. One method involves determining the levels of at least four markers in the blood of a patient, where at least two different markers are selected from CA-125, prolactin, HE4 (human epididymis protein 4), sV-CAM and TSH; and where a third marker and a fourth marker are selected from CA-125, prolactin, HE4, sV-CAM, TSH, cytokeratin, sI-CAM, IGFBP-1, eotaxin and FSH, where each of the third marker and fourth marker selected from the above listed markers is different from each other and different from either of the first and second markers, and where dysregulation of at least the four markers indicates high specificity and sensitivity for a diagnosis of ovarian cancer. Another panel includes at least eight markers in the blood of a patient, wherein at least four different markers are selected from the group consisting of CA-125, prolactin, HE4, sV-CAM, and TSH and wherein a fifth marker, a sixth marker, a seventh marker and an eighth marker are selected from the group consisting of CA-125, prolactin, HE4, sV-CAM, TSH, cytokeratin, sI-CAM, IGFBP-1, eotaxin and FSH, and further wherein each of said fifth marker, said sixth marker, said seventh marker and said eighth marker is different from the other and is different from any of said at least four markers, wherein dysregulation of said at least eight markers indicates high specificity and sensitivity for a diagnosis of ovarian cancer.

The Lokshin (2007) patent application also describes a blood marker panel comprising two or more of EGF (epidermal growth factor), G-CSF (granulocyte colony stimulating factor), IL-6, IL-8, CA-125 (Cancer Antigen 125), VEGF (vascular endothelial growth factor), MCP-I (monocyte chemoattractant protein-1), anti-IL6, anti-IL8, anti-CA-125, anti-c-myc, anti-p53, anti-CPA, anti-CA 15-3, anti-MUC-1, anti-survivin, anti-bHCG, anti-osteopontin, anti-PDGF, anti-Her2/neu, anti-Akt1, anti-cytokeratin 19, cytokeratin 19, EGFR, CEA, kallikrein-8, M-CSF, FasL, ErbB2 and Her2/neu in a sample of the patients blood, where the presence of two or more of the following conditions indicated the presence of ovarian cancer in the patient: EGF (low), G-CSF (high), IL-6 (high), IL-8 (high); VEGF (high), MCP-1 (low), anti-IL-6 (high), anti-IL-8 (high), anti-CA-125 (high), anti-c-myc (high), anti-p.sup.53 (high), anti-CEA (high), anti-CA 15-3 (high), anti-MUC-1 (high), anti-survivin (high), anti-bHCG (high), anti-osteopontin (high), anti-Her2/neu (high), anti-Akt1 (high), anti-cytokeratin 19 (high), anti-PDGF (high), CA-125 (high), cytokeratin 19 (high), EGFR (low, Hcr2/neu (low), CEA (high). FasL (high), kallikrein-8 (low), ErbB2 (low) and M-CSF (low). Exemplary panels include, without limitation: CA-125, cytokeratin-19. FasL, M-CSF; cytokeratin-19, CEA, Fas, EGFR, kallikrein-8; CEA, Fas, M-CSF, EGFR, CA-125; cytokeratin 19, kallikrein 8, CEA, CA 125, M-CSF; kallikrein-8, EGFR, CA-125; cytokeratin-19, CEA, CA-125, M-CSF, EGFR; cytokeratin-19, kallikrein-8, CA-125, M-CSF, FasL; cytokeratin-19, kallikrein-8, CEA, M-CSF; cytokeratin-19, kallikrein-8, CEA, CA-125; CA 125, cytokeratin 19, ErbB2; EGF, G-CSF, IL-6, IL-8, VEGF and MCP-1; anti-CA 15-3, anti-IL-8, anti-survivin, anti-p53 and anti c-myc; anti-CA 15-3, anti-IL-8, anti-survivin, anti-p53, anti c-myc, anti-CEA, anti-IL-6, anti-EGF; and anti-bHCG.

Chan, et al., "Use of biomarkers for detecting ovarian cancer," U.S. Published Patent Application 20050059013, published Mar. 17, 2005 describes a method of qualifying ovarian cancer status in a subject comprising: (a) measuring at least one biomarker in a sample from the subject, wherein the biomarker is selected from the group consisting of ApoA1, transthyretin .DELTA.N10, IAIH4 fragment, and combinations thereof, and (b) correlating the measurement with ovarian cancer status.

Another embodiment in the Chan application described an additional biomarker selected from CA125, CA125 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, for example, kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), osteopontin and haptoglobin, and protein variants (e.g., cleavage forms, isoforms) of the markers.

An ELISA-based blood serum test described the evaluation of four proteins useful in the early diagnosis of epithelial ovarian cancer (leptin, prolactin, osteopontin and insulin-like growth factor). The authors reported that no single protein could completely distinguish the cancer group from the healthy control group. However, the combination of these four proteins provided sensitivity 95%, positive predictive value (PPV) 95%, specificity 95%, and negative predictive value (NPV) 94%, which was said to be a considerable improvement on current methodology. Mor et al., "Serum protein markers for early detection of ovarian cancer," PNAS (102:21) 7677-7682 (2005).

A related patent application by Mor et al. "Identification of Cancer Protein Biomarkers Using Proteomic Techniques," U.S. Patent Application 2005/0214826, published Sep. 29, 2005 describes biomarkers identified by using a novel screening method. The biomarkers are stated to discriminate between cancer and healthy subjects as well as being useful in the prognosis and monitoring of cancer. Specifically, the abstract of the patent application relates to the use of leptin, prolactin, OPN and IGF-II for these purposes. The disclosed invention is somewhat more generally characterized as involving the comparison of expression of one or more biomarkers in a sample that are selected from the group consisting of: 6Ckine, ACE, BDNF, CA125, E-Selectin, EGF, Eot2, ErbB1, follistatin, HCC4, HVEM, IGF-II, IGFBP-1, IL-17, IL-1srII, IL-2sRa, leptin, M-CSF R, MIF, MIP-1a, MIP3b, MMP-8, MMP7, MPIF-1, OPN, PARC, PDGF Rb, prolactin, ProteinC, TGF-b RIII, TNF-R1, TNF-a, VAP-1, VEGF R2 and VEGF R3. A significant difference in the expression of these one or more biomarkers in the sample as compared to a predetermined standard of each is said to diagnose or aid in the diagnosis of cancer.

A patent application by Le Page et al. "Methods of Diagnosing Ovarian Cancer and Kits Therefor," WO2007/030949, published Mar. 22, 2007 describes a method for determining whether a subject is affected by ovarian cancer by detecting the expression levels of FGF-2 and CA125 and, optionally, IL-18.

Other approaches described in the patent and scientific literature include the analysis of expression of particular gene transcripts in blood cells. See, for example, Liew, "Method for the Detection of Cancer Related Gene Transcripts in Blood," U.S. Published Patent Application 2006/0134637, Jun. 22, 2006. Although gene transcripts specific for ovarian cancer are not identified, transcripts from Tables 3J, 3K and 3X are said to indicate the presence of cancer. See also, Tchagang et al., "Early Detection of Ovarian Cancer Using Group Biomarkers," Mol. Cancer Ther. (1):7 (2008).

Another diagnostic approach involves detecting circulating antibodies directed against tumor-associated antigens. See, Nelson et al. "Antigen Panels and Methods of Using the Same," U.S. Patent Application 2005/0221305, published Oct. 6, 2005; and Robertson "Cancer Detection Methods and Regents," U.S. Patent Application 2003/0232399, published Dec. 18, 2003.

What has been urgently needed in the field of gynecologic oncology is a minimally invasive (preferably serum-based) clinical test for assessing and predicting the presence of ovarian cancer that is based on a robust set of biomarkers and sample features identified from a large and diverse set of samples, together with methods and associated computer systems and software tools to predict, diagnose and monitor ovarian cancer with high accuracy at its various stages.

SUMMARY OF THE INVENTION

The present invention generally relates to cancer biomarkers and particularly to biomarkers associated with ovarian cancer. It provides methods to predict, evaluate diagnose, and monitor cancer, particularly ovarian cancer, by measuring certain biomarkers, and further provides a set or array of reagents to evaluate the expression levels of biomarkers that are associated with ovarian cancer. A preferred set of biomarkers provides a detectable molecular signature of ovarian cancer in a subject. The invention provides a predictive or diagnostic test for ovarian cancer, particularly for epithelial ovarian cancer and more particularly for early-stage ovarian cancer (that is Stage I, Stage II or Stage I and II together).

More specifically, predictive tests and associated methods and products also provide useful clinical information regarding the stage of ovarian cancer progression, that is: Stage I, Stage II, Stage III and Stage IV and an advanced stage which reflects relatively advanced tumors that cannot readily be classified as either Stage III or Stage IV. Overall, the invention also relates to newly discovered correlations between the relative levels of expression of certain groups of markers in bodily fluids, preferably blood serum and plasma, and a subject's ovarian cancer status.

In one embodiment, the invention provides a set of reagents to measure the expression levels of a panel or set of biomarkers in a fluid sample drawn from a patient, such as blood, serum, plasma, lymph, cerebrospinal fluid, ascites or urine. The reagents in a further embodiment are a multianalyte panel assay comprising reagents to evaluate the expression levels of these biomarker panels.

In embodiments of the invention, a subject's sample is prepared from tissue samples such a tissue biopsy or from primary cell cultures or culture fluid. In a further embodiment, the expression of the biomarkers is determined at the polypeptide level. Related embodiments utilize immunoassays, enzyme-linked immunosorbent assays and multiplexed immunoassays for this purpose.

Preferred panels of biomarkers are selected from the group consisting of the following sets of molecules and their measurable fragments: (a) myoglobin, CRP (C reactive protein), FGF basic protein and CA 19-9; (b) Hepatitis C NS4, Ribosomal P Antibody and CRP; (c) CA 19-9. TGF alpha, EN-RAGE, EGF and HSP 90 alpha antibody, (d) EN-RAGE, EGF, CA 125, Fibrinogen, Apolipoprotein CIII, EGF, Cholera Toxin and CA 19-9; (e) Proteinase 3 (cANCA) antibody, Fibrinogen, CA 125, EGF, CD40, TSH, Leptin, CA 19-9 and lymphotactin; (f) CA125, EGFR, CRP, IL-18, Apolipoprotein CIII, Tenascin C and Apolipoprotein A1; (g) CA125, Beta-2 Microglobulin, CRP, Ferritin, TIMP-1, Creatine Kinase-MB and IL-8; (h) CA125, EGFR, IL-10, Haptoglobin, CRP, Insulin, TIMP-1, Ferritin, Alpha-2 Macroglobulin, Leptin, IL-8, CTGF, EN-RAGE, Lymphotactin, TNF-alpha, IGF-1, TNF RII, von Willebrand Factor and MDC; (i) CA-125, CRP, EGF-R, CA-19-9, Apo-AI, Apo-CIII, IL-6, IL-18, MIP-1a, Tenascin C and Myoglobin; (j) CA-125, CRP, EGF-R, CA-19-9, Apo-AI, Apo-CIII, IL-6, MIP-1a, Tenascin C and Myoglobin; and (k) any of the biomarker panels presented in Table II and Table III.

In another embodiment, the reagents that measure such biomarkers may measure other molecular species that are found upstream or downstream in a biochemical pathway or measure fragments of such biomarkers and molecular species. In some instances, the same reagent may accurately measure a biomarker and its fragments.

Another embodiment of the present invention relates to binding molecules (or binding reagents) to measure the biomarkers and related molecules and fragments. Contemplated binding molecules includes antibodies, both monoclonal and polyclonal, aptamers and the like.

Other embodiments include such binding reagents provided in the form of a test kit, optionally together with written instructions for performing an evaluation of biomarkers to predict the likelihood of ovarian cancer in a subject.

In other of its embodiments, the present invention provides methods of predicting the likelihood of ovarian cancer in a subject based on detecting or measuring the levels in a specimen or biological sample from the subject of the foregoing biomarkers. As described in this specification, a change in the expression levels of these biomarkers, particularly their relative expression levels, as compared with a control group of patients who do not have ovarian cancer, is predictive of ovarian cancer in that subject.

In other of its aspects, the type of ovarian cancer that is predicted is serous, endometrioid, mucinous, and clear cell tumors. And prediction of ovarian cancer includes the prediction of a specific stage of the disease such as Stage I (IA, IB or IC), II, III and IV tumors.

In yet another embodiment, the invention relates to creating a report for a physician of the relative levels of the biomarkers and to transmitting such a report by mail, fax, email or otherwise. In an embodiment, a data stream is transmitted via the internet that contains the reports of the biomarker evaluations. In a further embodiment, the report includes the prediction as to the presence or absence of ovarian cancer in the subject or the stratified risk of ovarian cancer for the subject, optionally by subtype or stage of cancer.

According to another aspect of the invention, the foregoing evaluation of biomarker expression levels is combined for diagnostic purposes with other diagnostic procedures such as gastrointestinal tract evaluation, chest x-ray, HE4 test, CA-125 test, complete blood count, ultrasound or abdominal/pelvic computerized tomography, blood chemistry profile and liver function tests.

Yet other embodiments of the invention relate to the evaluation of samples drawn from a subject who is symptomatic for ovarian cancer or is at high risk for ovarian cancer. Other embodiments relate to subjects who are asymptomatic of ovarian cancer. Symptomatic subjects have one or more of the following: pelvic mass; ascites; abdominal distention; general abdominal discomfort and/or pain (gas, indigestion, pressure, swelling, bloating, cramps); nausea, diarrhea, constipation, or frequent urination; loss of appetite; feeling of fullness even after a light meal; weight gain or loss with no known reason; and abnormal bleeding from the vagina. The levels of biomarkers may be combined with the findings of such symptoms for a diagnosis of ovarian cancer.

Embodiments of the invention are highly accurate for determining the presence of ovarian cancer. By "highly accurate" is meant a sensitivity and a specificity each at least about 85 percent or higher, more preferably at least about 90 percent or 92 percent and most preferably at least about 95 percent or 97 percent accurate. Embodiments of the invention further include methods having a sensitivity of at least about 85 percent, 90 percent or 95 percent and a specificity of at least about 55 percent, 65 percent, 75 percent, 85 percent or 90 percent or higher. Other embodiments include methods having a specificity of at least about 85 percent, 90 percent or 95 percent, and a sensitivity of at least about 55 percent, 65 percent, 75 percent, 85 percent or 90 percent or higher.

Embodiments of the invention relating sensitivity and specificity are determined for a population of subjects who are symptomatic for ovarian cancer and have ovarian cancer as compared with a control group of subjects who are symptomatic for ovarian cancer but who do not have ovarian cancer. In another embodiment, sensitivity and specificity are determined for a population of subjects who are at increased risk for ovarian cancer and have ovarian cancer as compared with a control group of subjects who are at increased risk for ovarian cancer but who do not have ovarian cancer. And in another embodiment, sensitivity and specificity are determined for a population of subjects who are symptomatic for ovarian cancer and have ovarian cancer as compared with a control group of subjects who are not symptomatic for ovarian cancer but who do not have ovarian cancer.

In other aspects, the levels of the biomarkers are evaluated by applying a statistical method such as knowledge discovery engine (KDE™), regression analysis, discriminant analysis, classification tree analysis, random forests, ProteomeQuest®, support vector machine, One R, kNN and heuristic naive Bayes analysis, neural nets and variants thereof.

In another embodiment, a predictive or diagnostic model based on the expression levels of the biomarkers is provided. The model may be in the form of software code, computer readable format or in the form of written instructions for evaluating the relative expression of the biomarkers.

A patient's physician can utilize a report of the biomarker evaluation, in a broader diagnostic context, in order to develop a relatively more complete assessment of the risk that a given patient has ovarian cancer. In making this assessment, a physician will consider the clinical presentation of a patient, which includes symptoms such as a suspicious pelvic mass and/or ascites, abdominal distention and other symptoms without another obvious source of malignancy. The general lab workup for symptomatic patients currently includes a GI evaluation if clinically indicated, chest x-ray, CA-125 test, CBC, ultrasound or abdominal/pelvic CT if clinically indicated, chemistry profile with LFTs and may include a family history evaluation along with genetic marker tests such as BRCA-1 and BRCA-2. (See, generally, the NCCN Clinical Practice Guidelines in Oncology™ for Ovarian Cancer, V.1.2007.)

The present invention provides a novel and important additional source of information to assist a physician in stratifying a patient's risk of having ovarian cancer and in planning the next diagnostic steps to take. The present invention is also similarly useful in assessing the risk of ovarian cancer in non-symptomatic, high-risk subjects as well as for the general population as a screening tool. It is contemplated that the methods of the present invention may be used by clinicians as part of an overall assessment of other predictive and diagnostic indicators.

The present invention also provides methods to assess the therapeutic efficacy of existing and candidate chemotherapeutic agents and other types of cancer treatments. As will be appreciated by persons skilled in the art, the relative expression levels of the biomarker panels—or biomarker profiles—are determined as described above, in specimens taken from a subject prior to and again after treatment or, optionally, at progressive stages during treatment. A change in the relative expression of these biomarkers to a non-cancer profile of expression levels (or to a more nearly non-cancer expression profile) or to a stable, non-changing profile of relative biomarker expression levels is interpreted as therapeutic efficacy. Persons skilled in the art will readily understand that a profile of such expressions levels may become diagnostic for cancer or a pre-cancer, pre-malignant condition or simply move toward such a diagnostic profile as the relative ratios of the biomarkers become more like a cancer-related profile than previously.

In another embodiment, the invention provides a method for determining whether a subject potentially is developing cancer. The relative levels of expression of the biomarkers are determined in specimens taken from a subject over time, whereby a change in the biomarker expression profile toward a cancer profile is interpreted as a progression toward developing cancer.

The expression levels of the biomarkers of a specimen may be stored electronically once a subject's analysis is completed and recalled for such comparison purposes at a future time.

The present invention further provides methods, software products, computer systems and networks, and associated instruments that provide a highly accurate test for ovarian cancer.

The combinations of markers described in this specification provide sensitive, specific and accurate methods for predicting the presence of or detecting ovarian cancer at various stages of its progression. The evaluation of samples as described may also correlate with the presence of a pre-malignant or a pre-clinical condition in a patient. Thus, it is contemplated that the disclosed methods are useful for predicting or detecting the presence of ovarian cancer in a sample, the absence of ovarian cancer in a sample drawn from a subject, the stage of an ovarian cancer, the grade of an ovarian cancer, the benign or malignant nature of an ovarian cancer, the metastatic potential of an ovarian cancer, the histological type of neoplasm associated with the ovarian cancer, the indolence or aggressiveness of the cancer, and other characteristics of ovarian cancer that are relevant to prevention, diagnosis, characterization, and therapy of ovarian cancer in a patient.

It is further contemplated that the methods disclosed are also useful for assessing the efficacy of one or more test agents for inhibiting ovarian cancer, assessing the efficacy of a therapy for ovarian cancer, monitoring the progression of ovarian cancer, selecting an agent or therapy for inhibiting ovarian cancer, monitoring the treatment of a patient afflicted with ovarian cancer, monitoring the inhibition of ovarian cancer in a patient, and assessing the carcinogenic potential of a test compound by evaluating biomarkers of test animals following exposure.

DETAILED DESCRIPTION

The biomarker panels and associated methods and products were identified through the analysis of analyte levels of various molecular species in human blood serum drawn from subjects having ovarian cancer of various stages and subtypes, subjects having non-cancer gynecological disorders and normal subjects. The immunoassays described below were courteously performed by our colleagues at Rules-Based Medicine of Austin, Tex. using their Multi-Analyte Profile (MAP) Luminex® platform (www.rules-basedmedicine.com).

While a preferred sample is blood serum, it is contemplated that an appropriate sample can be derived from any biological source or sample, such as tissues, extracts, cell cultures, including cells (for example, tumor cells), cell lysates, and physiological fluids, such as, for example, whole blood, plasma, serum, saliva, ductal lavage, ocular lens fluid, cerebral spinal fluid, sweat, urine, milk, ascites fluid, synovial fluid, peritoneal fluid and the like. The sample can be obtained from animals, preferably mammals, more preferably primates, and most preferably humans using species specific binding agents that are equivalent to those discussed below in the context of human sample analysis. It is further contemplated that these techniques and marker panels may be used to evaluate drug therapy in rodents and other animals, including transgenic animals, relevant to the development of human and veterinary therapeutics.

The sample can be treated prior to use by conventional techniques, such as preparing plasma from blood, diluting viscous fluids, and the like. Methods of sample treatment can involve filtration, distillation, extraction, concentration, inactivation of interfering components, addition of chaotropes, the addition of reagents, and the like. Nucleic acids (including silencer, regulatory and interfering RNA) may be isolated and their levels of expression for the analytes described below also used in the methods of the invention.

Samples and Analytical Platform.

The set of blood serum samples that was analyzed to generate most of the data discussed below contained 150 ovarian cancer samples and 150 non-ovarian cancer samples. Subsets of these samples were used as described. The ovarian cancer sample samples further comprised the following epithelial ovarian cancer subtypes: serous (64), clear cell (22), endometrioid (35), mucinous (15), mixed, that is, consisting of more than one subtype (14). The stage distribution of the ovarian cancer samples was: Stage I (41), Stage II (23), Stage III (68), Stage IV (12) and unknown stage (6).

The non-ovarian cancer sample set includes the following ovarian conditions: benign (104), normal ovary (29) and "low malignant potential/borderline (3). The sample set also includes serum from patients with other cancers: cervical cancer (7), endometrial cancer (6) and uterine cancer (1).

Analyte levels in the samples discussed in this specification were measured using a high-throughput, multi-analyte immunoassay platform. A preferred platform is the Luminex® MAP system as developed by Rules-Based Medicine, Inc. in Austin, Tex. It is described on the company's website and also, for example, in publications such as Chandler et al., "Methods and kits for the diagnosis of acute coronary syndrome, U. S. Patent Application 2007/0003981, published Jan. 4, 2007, and a related application of Spain et al., "Universal Shotgun Assay," U. S. Patent Application 2005/0221363, published Oct. 6, 2005. This platform has previously been described in Lokshin (2007) and generated data used in other analyses of ovarian cancer biomarkers. However, any immunoassay platform or system may be used.

In brief, to describe a preferred analyte measurement system, the MAP platform incorporates polystyrene microspheres that are dyed internally with two spectrally distinct fluorochromes. By using accurate ratios of the fluorochromes, an array is created consisting of 100 different microsphere sets with specific spectral addresses. Each microsphere set can display a different surface reactant. Because microsphere sets can be distinguished by their spectral addresses, they can be combined, allowing up to 100 different analytes to be measured simultaneously in a single reaction vessel. A third fluorochrome coupled to a reporter molecule quantifies the biomolecular interaction that has occurred at the microsphere surface. Microspheres are interrogated individually in a rapidly flowing fluid stream as they pass by two separate lasers in the Luminex® analyzer. High-speed digital signal processing classifies the microsphere based on its spectral address and quantifies the reaction nil the surface in a few seconds per sample.

Skilled artisans will recognize that a wide variety of analytical techniques may be used to determine the levels of biomarkers in a sample as is described and claimed in this specification. Other types of binding reagents available to persons skilled in the art may be utilized to measure the levels of the indicated analytes in a sample. For example, a variety of binding agents or binding reagents appropriate to evaluate the levels of a given analyte may readily be identified in the scientific literature. Generally, an appropriate binding agent will bind specifically to an analyte, in other words, it reacts at a detectable level with the analyte but does not react detectably (or reacts with limited cross-reactivity) with other or unrelated analytes. It is contemplated that appropriate binding agents include polyclonal and monoclonal antibodies, aptamers, RNA molecules and the like. Spectrometric methods also may be used to measure the levels of analytes, including immunofluorescence, mass spectrometry, nuclear magnetic resonance and optical spectrometric methods. Depending on the binding agent to be utilized, the samples may be processed, for example, by dilution, purification, denaturation, digestion, fragmentation and the like before analysis as would be known to persons skilled in the art. Also, gene expression, for example, in a tumor cell or lymphocyte also may be determined.

It is also contemplated that the identified biomarkers may have multiple epitopes for immunoassays and/or binding sites for other types of binding agents. Thus, it is contemplated that peptide fragments or other epitopes of the identified biomarkers, isoforms of specific proteins and even compounds upstream or downstream in a biological pathway or that have been post-translationally modified may be substituted for the identified analytes or biomarkers so long as the relevant and relative stoichiometries are taken into account appropriately. Skilled artisans will recognize that alternative antibodies and binding agents can be used to determine the levels of any particular analyte, so long as their various specificities and binding affinities are factored into the analysis.

A variety of algorithms may be used to measure or determine the levels of expression of the analytes or biomarkers used in the methods and test kits of the present invention. It is generally contemplated that such algorithms will be capable of measuring analyte levels beyond the measurement of simple cut-off values. Thus, it is contemplated that the results of such algorithms will generically be classified as multivariate index analyses by the U.S. Food and Drug Administration. Specific types of algorithms include: knowledge discovery engine (KDE™), regression analysis, discriminant analysis, classification tree analysis, random forests, ProteomeQuest®, support vector machine, One R, kNN and heuristic naive Bayes analysis, neural nets and variants thereof.

ANALYSIS AND EXAMPLES

The following discussion and examples are provided to describe and illustrate the present invention. As such, they should not be construed to limit the scope of the invention. Those skilled in the art will well appreciate that many other embodiments also fall within the scope of the invention, as it is described in this specification and the claims.

Analysis of Data to Find Informative Biomarker Panels Using the KDE™.

Correlogic has described the use of evolutionary and pattern recognition algorithms in evaluating complex data sets, including the Knowledge Discovery Engine (KDE™) and ProteomeQuest®. See, for example, Hitt et al., U.S. Pat. No. 6,925,389, "Process for Discriminating Between Biological States Based on Hidden Patterns From Biological Data" (issued Aug. 2, 2005); Hitt, U.S. Pat. No. 7,096,206, "Heuristic Method of Classification," (issued Aug. 22, 2006) and Hitt, U.S. Pat. No. 7,240,038, "Heuristic Method of Classification," (to be issued Jul. 3, 2007). The use of this technology to evaluate mass spectral data derived from ovarian cancer samples is further elucidated in Hitt et al., "Multiple high-resolution serum proteomic features for ovarian cancer detection." U. S. Published Patent Application 2006/0064253, published Mar. 23, 2006.

When analyzing the data set by Correlogic's Knowledge Discovery Engine, the following five-biomarker panels were found to provide sensitivities and specificities for various stages of ovarian cancer as set forth in Table 1. Specifically, KDE Model 1 [2_0008_20] returned a relatively high accuracy for Stage I ovarian cancer and included these markers: Cancer Antigen 19-9 (CA19-9, Swiss-Prot Accession Number: Q9RX19), C Reactive Protein (CRP, Swiss-Prot Accession Number: P02741), Fibroblast Growth Factor-basic Protein (FGF-basic, Swiss-Prot Accession Number: P09038) and Myoglobin (Swiss-Prot Accession Number: P02144). KDE Model 2 [4_0002_10] returned a relatively high accuracy for Stage III, IV and "advanced" ovarian cancer and included these markers: Hepatitis C NS4 Antibody (Hep C NS4 Ab), Ribosomal P Antibody and CRP. KDE. Model 3 [4_0009_140] returned a relatively high accuracy for Stage I and included these markers: C.A. 19-9, TGF alpha, EN- RAGE (Swiss-Prot Accession Number: P80511), Epidermal Growth Factor (EGF. Swiss-Prot Accession Number: P01133) and HSP 90 alpha antibody. KDE Model 4 [4_0026_100] returned a relatively high accuracy for Stage II and Stages III, IV and "advanced" ovarian cancers and included these markers: EN-RAGE, EGF. Cancer Antigen 125 (CA125, Swiss-Prot Accession Number: Q14596), Fibrinogen (Swiss-Prot Accession Number: Alpha chain P02671; Beta chain P02675; Gamma chain P02679), Apolipoprotein CIII (ApoCIII, Swiss-Prot Accession Number: P02656), Cholera Toxin and CA 19-9. KDE Model 5 [4_0027_ 20] also returned a relatively high accuracy for Stage II and Stages III, IV and "advanced" ovarian cancers and included these markers: Proteinase 3 (cANCA) antibody. Fibrinogen, CA 125, EGF, CD40 (Swiss-Prot Accession Number: Q6P2H9), Thyroid Stimulating Hormone (TSH. Swiss-Prot Accession Number: Alpha P01215; Beta P01222 P02679, Leptin (Swiss-Prot Accession Number: P41159), CA 19-9 and Lymphotactin (Swiss-Prot Accession Number: P47992). It is contemplated that skilled artisans could use the KDE analytical tools to identify other, potentially useful sets of biomarkers for predictive or diagnostic value based on the levels of selected analytes. Note that the KDE algorithm may select and utilize various markers based on their relative abundances; and that a given marker, for example the level of cholera toxin in Model IV may be zero but is relevant in combination with the other markers selected in a particular grouping.

Skilled artisans will recognize that a limited size data set as was used in this specification may lead to different results, for example, different panels of markers and varying accuracies when comparing the relative performance of KDE with other analytical techniques to identify informative panels of biomarkers. These particular KDE models were built on a relatively small data set using 40 stage I ovarian cancers and 40 normal/benigns and were tested blindly on the balance of the stage II, III/IV described above. Thus, the specificity is of the stage I samples reflects sample set size and potential overfitting. The drop in specificity for the balance of the non-ovarian cancer samples also is expected given the relatively larger size of the testing set relative to the training set. Overall, the biomarker panel developed for the stage I samples also provides potentially useful predictive and diagnostic assays for later stages of ovarian cancer given the high sensitivity values.

However, these examples of biomarker panels illustrate that there are a number of parameters that can be adjusted to impact model performance. For instance in these cases a variety of different numbers of features are combined together, a variety of match values are used, a variety of different lengths of evolution of the genetic algorithm are used and models differing in the number of nodes are generated. By routine experimentation apparent to one skilled in the art, combinations of these parameters can be used to generate other predictive models based on biomarker panels having clinically relevant performance.

TABLE 1

Results of Analysis Using Knowledge Discovery Engine to develop a stage I specific classification model.

| Model Name | Feature | Match | Generation | Node | Sensitivity Stage I | Specificity Stage I | Accuracy Stage I | Sensitivity Stage II | Sensitivity Stage III-IV | Specificity |
|---|---|---|---|---|---|---|---|---|---|---|
| 2_0008_20 | 4 | 0.9 | 20 | 12 | 75 | 100 | 87.5 | 60.9 | 46.5 | 82.6 |
| 4_0002_10 | 3 | 0.7 | 10 | 4 | 75 | 100 | 87.5 | 69.6 | 82.6 | 56 |
| 4_0009_140 | 5 | 0.6 | 140 | 5 | 75 | 100 | 87.5 | 43.5 | 39.5 | 71.6 |
| 4_0026_100 | 9 | 0.7 | 100 | 5 | 87.5 | 100 | 93.8 | 78.3 | 84.9 | 67 |
| 4_0027_20 | 9 | 0.8 | 20 | 5 | 87.5 | 100 | 93.8 | 78.3 | 84.9 | 60.6 |

Methods and Analysis to Find Informative Biomarker Panels Using Random Forests.

A preferred analytical technique, known to skilled artisans, is that of Breiman, Random Forests. Machine Learning, 2001. 45:5-32; as further described by Segel, Machine Learning Benchmarks and Random Forest Regression, 2004; and Robnik-Sikonja, Improving Random Forests, in Machine Learning, ECML, 2004 Proceedings, J. F. B. e. al., Editor, 2004, Springer: Berlin. Other variants of Random Forests are also useful and contemplated for the methods of the present invention, for example, Regression Forests, Survival Forests, and weighted population Random Forests.

A modeling set of samples was used as described above for diagnostic models built with the KDE algorithm. Since each of the analyte assays is an independent measurement of a variable, under some circumstances, known to those skilled in the art, it is appropriate to scale the data to adjust for the differing variances of each assay. In such cases, biweight, MAD or equivalent scaling would be appropriate, although in some cases, scaling would not be expected to have a significant impact. A bootstrap layer on top of the Random Forests was used in obtaining the results discussed below.

In preferred embodiments of the present invention, contemplated panels of biomarkers are:

a. Cancer Antigen 125 (CA125, Swiss-Prot Accession Number: Q14596) and Epidermal Growth Factor Receptor (EGF-R, Swiss-Prot Accession Number: P00533).

b. CA125 and C Reactive Protein (CRP, Swiss-Prot Accession Number: P02741).

c. CA125, CRP and EGF-R.

d. Any one or more of CA125, CRP and EGF-R, plus any one or more of Ferritin (Swiss-Prot Accession Number: Heavy chain P02794; Light chain P02792), Interleukin-8 (IL-8, Swiss-Prot Accession Number: P10145), and Tissue Inhibitor of Metalloproteinases 1 (TEMP-1, Swiss-Prot Accession Number: P01033), e. Any one of the biomarker panels presented in Table II and fable Ill.

f. Any of the foregoing panels of biomarkers (a-e) plus any one or more of the other biomarkers in the following list if not previously included in the foregoing panels (a-e). These additional biomarkers were identified empirically or by a literature review: Alpha-2 Macroglobulin (A2M, Swiss-Prot Accession Number: P01023), Apolipoprotein A1-1 (ApoA1, Swiss-Prot Accession Number: P02647), Apolipoprotein (ApoCIII, Swiss-Prot Accession Number: P02656), Apolipoprotein H (ApoH, Swiss-Prot Accession Number: P02749), Beta-2 Microglobulin (B2M, Swiss-Prot Accession Number: P23560), Betacellulin (Swiss-Prot Accession Number: P35070), C Reactive Protein (CRP, Swiss-Prot Accession Number: P02741). Cancer Antigen 19-9 (CA19-9, Swiss-Prot Accession Number: Q9BXJ9), Cancer Antigen 125 (CA125, Swiss-Prot Accession Number: Q14596), Collagen Type 2 Antibody, Creatine Kinase-MB (CK-MB, Swiss-Prot Accession Number: Brain P12277; Muscle P06732), C Reactive Protein (CRP, Swiss-Prot Accession Number: P02741), Connective Tissue Growth Factor (CTGF, Swiss-Prot Accession Number: P29279), Double Stranded DNA Antibody (dsDNA Ab), EN-RAGE (Swiss-Prot Accession Number: P80511), Eotaxin (C-C motif chemokine 11, small-inducible cytokine A11 and Eosinophil chemotactic protein, Swiss-Prot Accession Number: P51671), Epidermal Growth Factor Receptor (EGF-R, Swiss-Prot Accession Number: P00533), Ferritin (Swiss-Prot Accession Number: Heavy chain P02794; Light chain P02792), Follicle-stimulating hormone (FSH, Follicle-stimulating hormone beta subunit, FSH-beta, FSH-B, Follitropin beta chain, Follitropin subunit beta, Swiss-Prot Accession Number: P01225), Haptoglobin (Swiss-Prot Accession Number: P00738), HE4 (Major epididymis-specific protein E4, Epididymal secretory protein E4, Putative protease inhibitor WAP5 and WAP four-disulfide core domain protein 2, Swiss-Prot Accession Number: Q14508), Insulin (Swiss-Prot Accession Number: P01308), Insulin-like Growth Factor 1 (IGF-1, Swiss-Prot Accession Number: P01343), Insulin like growth factor II (IGF-II, Somatomedin-A, Swiss-Prot Accession Number: P01344), Insulin Factor VII (Swiss-Prot Accession Number: P08709), Interleukin-6 (IL-6, Swiss-Prot Accession Number: P05231), Interleukin-8 (IL-8, Swiss-Prot Accession Number: P10145), Interleukin-10 (IL-10, Swiss-Prot Accession Number: P22301), Interleukin-18 (IL-18, Swiss-Prot Accession Number: Q14116), Leptin (Swiss-Prot Accession Number: P41159), Lymphotactin (Swiss-Prot Accession Number: P47992), Macrophage-derived Chemokine (MDC, Swiss-Prot Accession Number: 000626), Macrophage Inhibotory Factor (SWISS PROT), Macrophage Inflammatory Protein 1 alpha (MIP-1alpha, Swiss-Prot Accession Number: P10147), Macrophage migration inhibitory factor (MIF, Phenylpyruvate tautomerase, Glycosylation-inhibiting factor, GIF, Swiss-Prot Accession Number: P14174), Myoglobin (Swiss-Prot Accession Number: P02144), Ostopontin (Bone sialoprotein 1, Secreted phosphoprotein 1, SPP-1, Urinary stone protein, Nephropontin, Uropontin, Swiss-Prot Accession Number: P10451), Pancreatic Islet Cells (GAD) Antibody, Prolactin (Swiss-Prot Accession Number: P01236), Stem Cell Factor (SCF, Swiss-Prot Accession Number: P21583), Tenascin C (Swiss-Prot Accession Number: P24821), Tissue Inhibitor of Metalloproteinases 1 (TIMP-1, Swiss-Prot Accession Number: P01033), Tumor Necrosis Factor-alpha (TNF-alpha, Swiss-Prot Accession Number: P01375), Tumor Necrosis Factor RII (TNF-RII, Swiss-Prot Accession Number: Q92956), von Willebrand Factor (vWF, Swiss-Prot Accession Number: P04275) and the other biomarkers identified as being informative for cancer in the references cited in this specification.

Using the Random Forests analytical approach, a preferred seven biomarker panel was identified that has a high predictive value for Stage I ovarian cancer. It includes: ApoAI, ApoCIII, CA125, CRP, EGF-R, IL-18 and Tenascin. In the course of building and selecting the relatively more accurate models for Stage I cancers generated by Random Forests using these biomarkers, the sensitivity for Stage I ovarian cancers ranged from about 80% to about 85%. Sensitivity was also about 95 for Stage II and about 94% sensitive for Stage III/IV. The overall specificity was about 70%.

Similarly, a preferred seven biomarker panel was identified that has a high predictive value for Stage II. It includes: B2M, CA125, CK-MB, CRP, Ferritin, IL-8 and TIMP1. A preferred model for Stage II had a sensitivity of about 82% and a specificity of about 88%.

For Stage III, Stage IV and advanced ovarian cancer, the following 19 biomarker panel was identified: A2M, CA125, CRP, CTGF, EGF-R, EN-RAGE, Ferritin, Haptoglobin, IGF-1, IL-8, IL-10, Insulin, Leptin, Lymphotactin, MDC, TEMP-1, TNF-alpha, TNF-RII, vWF. A preferred model for Stage III/IV had a sensitivity of about 86% and a specificity of about 89%.

Other preferred biomarker or analyte panels for detecting, diagnosing and monitoring ovarian cancer are shown in Table II and in Table III. These panels include CA-125, CRP and EGF-R and, in most cases, CA19-9. In Table II, 20 such panels of seven analytes each selected from 20 preferred analytes are displayed in columns numbered 1 through 20. In Table III, another 20 such panels of seven analytes each selected from 23 preferred analytes are displayed in columns numbered 1 through 20.

TABLE II

| | Additional Biomarker Panels | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| CA125 | x | x | x | x | x | x | x | x | x | x | x | x | x | x | x | x | x | x | x | x |
| CRP | x | x | x | x | x | x | x | x | x | x | x | x | x | x | x | x | x | x | x | x |
| EGF-R | x | x | x | x | x | x | x | x | x | x | x | x | x | x | x | x | x | x | x | x |
| CA19-9 | x | x | x | x | x | x | x | x | x | | x | x | x | x | x | x | x | x | x | x |
| Haptoglobin | | | | | | | | | | | | | | | | | | | | |
| Serum Amyloid P | | x | | x | | x | | | | | | | | | | | | | | |
| Apo AI | | | | | x | x | | | | | | | | | | | | | | |
| IL-6 | | x | x | | | x | | x | | | | | | | | | | x | | x |
| Myoglobin | | | x | | | x | x | x | | x | x | x | x | x | x | x | | | | |
| MIP-1α | x | x | x | x | | x | x | x | x | x | x | x | | | | x | | | | |
| EN-RAGE | | | | | | | | | | | | | | | | | | | | |
| CK-MB | | | | | | | | | | | | | | | | | | | | |
| vWF | x | x | | x | | | | | | | | | | | | | | | | |
| Leptin | | | | | | | | | | | | | | | x | x | | | | |
| Apo CIII | | | | x | x | | | | | | | | | | | | | x | | |
| Growth Hormone | | | | | | | x | | | x | x | x | | | x | x | | | | |
| IL-10 | | | | | | | | | | | | | | | | | | | | |
| IL-18 | x | | x | x | x | | | x | | x | | | | | | | | x | x | |
| Myeloperoxidase | | | | | | x | | | | | x | | | | | | | | | |
| VCAM-1 | x | x | | | | | | | | | | | x | | | | | | | |

TABLE III

| | Additional Biomarker Panels | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| CA125 | x | x | x | x | x | x | x | x | x | x | x | x | x | x | x | x | x | x | x | x |
| CRP | x | x | x | x | x | x | x | x | x | x | x | x | x | x | x | x | x | x | x | x |
| EGF-R | x | x | x | x | x | x | x | x | x | x | x | x | x | x | x | x | x | x | x | x |
| CA19-9 | x | x | x | x | x | x | x | x | x | x | x | | x | x | x | x | x | x | x | x |
| Haptoglobin | | | | | | | | | | | | | | | | | | | | |
| Serum Amyloid P | | | x | | | | | | | | | x | | | | | x | | | |
| Apo AI | | x | | | | x | | | | | | | | | | | | | | |
| IL-6 | | | | | | | | | | | x | x | | x | x | | | x | x | |
| Myoglobin | x | x | x | x | x | x | x | x | x | x | | | | | | | | | | |
| MIP-1α | x | | x | x | x | x | x | x | x | | | x | | x | x | | | x | | x |
| EN-RAGE | | | | | | | | | | | | | | | | | | | | |
| CK-MB | | | | | | | | | | | | | | | | | | | x | |
| vWF | | | | | | | | | | | | x | x | | x | | | | x | |
| Leptin | x | x | | | | x | | | | | | | | | | | | | | |
| Apo CIII | | | | x | | x | x | | | | | | | | | x | x | x | | |
| Growth Hormone | | | | | | | | | | | | | | | | | | | | |
| IL-10 | | | | | | | | | | | | | | | x | | | | | x |
| IL-18 | | | | | | | | | | | | | | | | | | | | |
| Myeloperoxidase | x | | | x | | | | | | | | x | | | | | | | | |
| VCAM-1 | | | | | | | | | | | | | | | | | | | | |
| Insulin | | | x | | | | | | | | | | | | | | | | | |
| Ferritin | | | x | | | | | | | | | x | x | | | | x | | | x |
| Haptoglobin | | | | | x | | | | | | | | | | | | | | | |

Other preferred biomarker panels (or models) for all stages of ovarian cancer include: (a) CA-125, CRP, EGF-R, CA-19-9, Apo-AI, Apo-CIII, IL-6, IL-18, MIP-1a, Tenascin C and Myoglobin; (b) CA125, CRP, CA19-9, EGF-R, Myoglobin, IL-18, Apo CIII; and (e) CA125, CRP, EGF-R, CA19-9, Apo CIII, MTP-1a, Myoglobin, IL-18, IL-6, Apo AI, Tenascin C, vWF, Haptoglobin, IL-10. Optionally, any one or more of the following biomarkers may be added to these or to any of the other biomarker panels disclosed above in text or tables (to the extent that any such panels are not already specifically identified therein): vWF, Haptoglobin, IL-10, IGF-I, IGF-II, Prolactin, HE4, ACE, ASP and Resistin.

Any two or more of the preferred biomarkers described above will have predictive value, however, adding one or more of the other preferred markers to any of the analytical panels described herein may increase the panel's predictive value for clinical purposes. For example, adding one or more of the different biomarkers listed above or otherwise identified in the references cited in this specification may also increase the biomarker panel's predictive value and are therefore expressly contemplated. Skilled artisans can readily assess the utility of such additional biomarkers. It is contemplated that additional biomarker appropriate for addition to the sets (or panels) of biomarkers disclosed or claimed in this specification will not result in a decrease in either sensitivity or specificity without a corresponding increase in either sensitivity or specificity or without a corresponding increase in robustness of the biomarker panel overall. A sensitivity and/or specificity of at least about 80% or higher are preferred, more preferably at least about 85% or higher, and most preferably at least about 90% or 95% or higher.

To practice the methods of the present invention, appropriate cut-off levels for each of the biomarker analytes must be determined for cancer samples in comparison with control samples. As discussed above, it is preferred that at least about 40 cancer samples and 40 benign samples (including benign, non-malignant disease and normal subjects) be used for this purpose, preferably case matched by age, sex and gender. Larger sample sets are preferred. A person skilled in the art would measure the level of each biomarker in the selected biomarker panel and then use an algorithm, preferably such as Random Forest, to compare the level of analytes in the cancer samples with the level of analytes in the control samples. In this way, a predictive profile can be prepared based on informative cutoffs for the relevant disease type. The use of a separate validation set of samples is preferred to confirm the cut-off values so determined. Case and control samples can be obtained by obtaining consented (or anonymized) samples in a clinical trial or from repositories like the Screening Study for Prostate, Lung. Colorectal, and Ovarian Cancer—PLCO Trial sponsored by the National Cancer Institute (http://www.cancer.gov/clinicaltrials/PLCO-1) or The Gynecologic Oncology Group (http://www.gog.org/). Samples obtained in multiple sites are also preferred.

The results of analysis of patients' specimens using the disclosed predictive biomarker panels may be output for the benefit of the user or diagnostician, or may otherwise be displayed on a medium such as, but not limited to, a computer screen, a computer readable medium, a piece of paper, or any other visible medium.

The foregoing embodiments and advantages of this invention are set forth, in part, in the preceding description and examples and, in part, will be apparent to persons skilled in the art from this description and examples and may be further realized from practicing the invention as disclosed herein. For example, the techniques of the present invention are readily applicable to monitoring the progression of ovarian cancer in an individual, by evaluating a specimen or biological sample as described above and then repeating the evaluation at one or more later points in time, such that a difference in the expression or disregulation of the relevant biomarkers over time is indicative of the progression of the ovarian cancer in that individual or the responsiveness to therapy. All references, patents, journal articles, web pages and other documents identified in this patent application are hereby incorporated by reference in their entireties.

OVARIAN CANCER BIOMARKERS—REFERENCES

1. Ahmed, N., et al., Proteomic-based identification of haptoglobin-1 precursor as a novel circulating biomarker of ovarian cancer. Br J Cancer, 2004. 91(1): p. 129-40.
2. Ahmed, N., et al., Cell-free 59 kDa immunoreactive integrin-linked kinase: a novel marker for ovarian carcinoma. Clin Cancer Res, 2004. 10(7): p. 2415-20.
3. Ahmed, N., et al., Proteomic tracking of serum protein isoforms as screening biomarkers of ovarian cancer. Proteomics, 2005. 5(17): p. 4625-36.
4. Akcay, T., et al., Significance of the O6-methylguanine-DNA methyltransferase and glutathione S-transferase activity in the sera of patients with malignant and benign ovarian tumors. Eur J Obstet Gynecol Reprod Biol, 2005. 119(1): p. 108-13,
5. An, H. J., et al., Profiling of glycans in serum for the discovery of potential biomarkers for ovarian cancer. J Proteome Res, 2006. 5(7): p. 1626-35.
6. Baron, A. T., et al., Soluble epidermal growth factor receptor (sEGFR) [corrected] and cancer antigen 125 (CA125) as screening and diagnostic tests for epithelial ovarian cancer. Cancer Epidemiol Biomarkers Prev, 2005. 14(2): p. 306-18.
7. Baron-Hay, S., et al., Elevated serum insulin-like growth factor binding protein-2 as a prognostic marker in patients with ovarian cancer. Clin Cancer Res, 2004. 10(5): p. 1796-806.
8. Bast, R. C., Jr.; et al., Prevention and early detection of ovarian cancer: mission impossible? Recent Results Cancer Res, 2007. 174: p. 91-100.
9. Ben-Arie, A., et al., Elevated serum alkaline phosphatase may enable early diagnosis of ovarian cancer. Eur J Obstet Gynecol Reprod Biol, 1999. 86(1): p. 69-71.
10. Bergen, H. R., 3rd, et al., Discovery of ovarian cancer biomarkers in serum using NanoLC electrospray ionization TOF and FT-ICR mass spectrometry. Dis Markers, 2003. 19(4-5): p. 239-49.
11. Bignotti, E., et al., Gene expression profile of ovarian serous papillary carcinomas: identification of metastasis-associated genes. Am J Obstet Gynecol, 2007. 196(3): p. 245 e1-11.
12. Boran, N., et al., Significance of serum and peritoneal fluid lactate dehydrogenase levels in ovarian cancer. Gynecol Obstet Invest, 2000. 49(4): p. 272-4.
13. Chen, Y. D., et al., Artificial neural networks analysis of surface-enhanced laser desorption/ionization mass spectra of serum protein pattern distinguishes colorectal cancer from healthy population. Clin Cancer Res, 2004. 10(24): p. 8380-5.
14. Chen, Y. D., et al., [Application of serum protein pattern model in diagnosis of colorectal cancer]. Zhonghua Zhong Liu Za Zhi, 2004. 26(7): p. 417-20.
15. Chatterjee, M., et al., Diagnostic markers of ovarian cancer by high-throughput antigen cloning and detection on arrays. Cancer Res, 2006. 66(2): p. 1181-90.
16. Clarke, C. H., et al., Proteomics discovery of urinary biomarkers for early stage ovarian cancer, in 2007 Annual Meeting of AACR Conference. 2007: Los Angeles Convention Center, LA, CA.
17. Conover, C. A. and K. R. Kalli, Methods of detecting ovarian neoplasia. 2005: USA.
18. Cox, C. J., R. G. Freedman, and H. A. Fritsche, Lacto-N-fucopentaose III activity in the serum of patients with ovarian carcinoma. Gynecol Obstet Invest, 1986. 21(3): p. 164-8.
19. Devine, P. L., at al., Serum mucin antigens CASA and MSA in tumors of the breast, ovary, lung, pancreas, bladder, colon, and prostate. A blind trial with 420 patients. Cancer, 1993. 72(6): p. 2007-15.
20. Dhokia, B., et al., A new immunoassay using monoclonal antibodies IIMFG1 and HMFG2 together with an existing marker CA125 for the serological detection and management of epithelial ovarian cancer. Br J Cancer, 1986. 54(6): p. 891-5.
21. Diefenbach, C. S., et al., Preoperative serum YKL-40 is a marker for detection and prognosis of endometrial cancer. Gynecol Oncol, 2007. 104(2): p. 435-42.
22. Draghici, S., M. Chatterjee, and M. A. Tainsky, Epitomics: serum screening for the early detection of cancer on microarrays using complex panels of tumor antigens. Expert Rev Mol Diagn, 2005. 5(5): p. 735-43.
23. Einhorn, N., et al., CA 125 assay used in conjunction with CA 15-3 and TAG-72 assays for discrimination between malignant and non-malignant diseases of the ovary. Acta Oncol, 1989. 28(5): p. 655-7.
24. Erkanli, A., et al., Application of Bayesian modeling of autologous antibody responses against ovarian tumor-associated antigens to cancer detection. Cancer Res, 2006. 66(3): p. 1792-8.
25. Fioretti, P., et al., Preoperative evaluation of CA 125 and CA 19-9 serum levels in patients with ovarian masses. Eur J Gynaecol Oncol, 1988. 9(4): p. 291-4.
26. Fung, E. T., et al. Novel biomarkers to aid in the differential diagnosis of a pelvic mass. in IGCS Conference. 2006. Santa, Monica, Calif.
27. Fung, E. T., et al., Classification of cancer types by measuring variants of host response proteins using SELDI serum assays. Int J Cancer, 2005. 115(5): p. 783-9.
28. Fung(a), E. T., et al. Novel biomarkers that predict survival in patients with ovarian cancer. 2006.
29. Gadducci, A., et al., The serum concentrations of TAG-72 antigen measured with CA 72-4 IRMA in patients with ovarian carcinoma. Preliminary data. J Nucl Med Allied Sci, 1989. 33(1): p. 32-6.
30. Gorelik, E., et al., Multiplexed immunobead-based cytokine profiling for early detection of ovarian cancer. Cancer Epidemiol Biomarkers Prev, 2005. 14(4): p. 981-7.
31. Hellstrom, I., et al., Mesothelin variant 1 is released from tumor cells as a diagnostic marker. Cancer Epidemiol Biomarkers Prev, 2006. 15(5): p. 1014-20.
32. Ibanez de Caceres, I., et al., Tumor cell-specific BRCA1 and RASSF1A hypermethylation in serum, plasma, and peritoneal fluid from ovarian cancer patients. Cancer Res. 2004. 64(18): p. 6476-81.
33. Inoue. M., et al., Sialyl Lewis-Xi antigen in patients with gynecologic tumors. Obstet Gynecol, 1989. 73(1): p. 79-83.
34. Inoue, M., et al., [The clinical value of sialyl SSEA-1 antigen in patients with gynecologic tumors]. Nippon Sanka Fujinka Gakkai Zasshi, 1987. 39(12): p. 2120-4.
35. Kizawa, I., Y. Kikuchi, and K. Kato, [Diagnostic value of biochemical tumor markers in serum of patients with cancer of the ovary]. Nippon Sanka Fujinka Gakkai Zasshi, 1983. 35(3): p. 251-8.
36. Knauf, S., et al., A study of the NB/7OK and CA 125 monoclonal antibody radioimmunoassays for measuring serum antigen levels in ovarian cancer patients. Am J Obstet Gynecol, 1985. 152(7 Pt 1): p. 911-3.
37. Kobayashi, H., T. Terao, and Y. Kawashima, Clinical evaluation of circulating serum sialyl Tn antigen levels in patients with epithelial ovarian cancer. J Clin Uncut, 1991. 9(6): p. 983-7.

38. Koelbl, H., et al., A comparative study of mucin-like carcinoma-associated antigen (MCA), CA 125, CA 19-9 and CEA in patients with ovarian cancer. Neoplasma, 1989. 36(4): p. 473-8.

39. Koivunen, E., et al., Cyst fluid of ovarian cancer patients contains high concentrations of trypsinogen-2. Cancer Res, 1990. 50(8): p. 2375-8.

40. Kong. F., et al., Using proteomic approaches to identify new biomarkers for detection and monitoring of ovarian cancer. Gynecol Oncol, 2006. 100(2): p. 247-53.

41. Kozak, K. R., et al., Identification of biomarkers for ovarian cancer using strong anion-exchange ProteinChips: potential use in diagnosis and prognosis. Proc Natl Acad Sci USA, 2003. 100(21): p. 12343-8.

42. Kozak, K. R., et al., Characterization of serum biomarkers for detection of early stage ovarian cancer. Proteomics, 2005. 5(17): p. 4589-96.

43. Lambeck, A. J., et al., Serum Cytokine Profiling as a Diagnostic and Prognostic Tool in Ovarian Cancer: A Potential Role for Interleukin 7. Clin Cancer Res. 2007. 13(8): p. 2385-2391.

44. Le Page, C., et A. From gene profiling to diagnostic markers: IL-18 and FGF-2 complement CA125 as serum-based markers in epithelial ovarian cancer. Int J Cancer, 2006. 118(7): p. 1750-8.

45. Lim, R., et al., Neutrophil gelatinase-associated lipocalin (NGAL) an early-screening biomarker for ovarian cancer: NGAL is associated with epidermal growth factor-induced epithelio-mesenchymal transition. Int J Cancer, 2007. 120 (11): p. 2426-34.

46. Lin, Y. W., et al., Plasma proteomic pattern as biomarkers for ovarian cancer. Int J Gynecol Cancer, 2006. 16 Suppl 1: p. 139-46.

47. Lokshin, A., Enhanced diagnostic multimarker serological profiling. 2007: USA.

48. Lokshin, A. E., et al., Circulating IL-8 and anti-IL-8 autoantibody in patients with ovarian cancer. Gynecol Oncol, 2006. 102(2): p. 244-51.

49. Lopez, M. F., et al., A novel, high-throughput workflow for discovery and identification of serum carrier protein-bound Peptide biomarker candidates in ovarian cancer samples. Clin Chem, 2007. 53(6): p. 1067-74.

50. Malki, S., et al., Expression and biological role of the prostaglandin D synthase/SOX9 pathway in human ovarian cancer cells. Cancer Lett, 2007.

51. Massi, G. B., et al., The significance of measurement of several oncofetal antigens in diagnosis and management of epithelial ovarian tumors. Eur J Gynaecol Oncol, 1983. 4(2): p. 88-93.

52. Meden, H., et al., Elevated serum levels of a c-erbB-2 oncogene product in ovarian cancer patients and in pregnancy. J Cancer Res Clin Oncol, 1994. 120(6): p. 378-81.

53. Mehta, A. I., et al., Biomarker amplification by serum carrier protein binding. Dis Markers, 2003. 19(1): p. 1-10.

54. Meinhold-Heerlein, I., et al., An integrated clinical-genomics approach identifies a candidate multi-analyte blood test for serous ovarian carcinoma. Clin Cancer Res, 2007. 13(2 Pt 1): p. 458-66.

55. Miszczak-Zaborska, E., et al., The activity of thymidine phosphorylase as a new ovarian tumor marker. Gynecol Oncol, 2004. 94(1): p. 86-92.

56. Moore, L. E., et al., Evaluation of apolipoprotein A1 and posttranslationally modified forms of transthyretin as biomarkers for ovarian cancer detection in an independent study population. Cancer Epidemic)! Biomarkers Prev, 2006. 15(9): p. 1641-6.

57. Mor, G., et al., Serum protein markers for early detection of ovarian cancer. Proc Natl Acad Sci USA, 2005. 102(21): p. 7677-82.

58. Moscova, M., D. J. Marsh, and R. C. Baxter, Protein chip discovery of secreted proteins regulated by the phosphatidylinositol 3-kinase pathway in ovarian cancer cell lines. Cancer Res, 2006. 66(3): p. 1376-83.

59. Nakae, M., et al., Preoperative plasma osteopontin level as a biomarker complementary to carbohydrate antigen 125 in predicting ovarian cancer. J Obstet Gynaecol Res, 2006. 32(3): p. 309-14.

60. Nozawa, S., et al., [Galactosyltransferase isozyme II (GT-II) as a new tumor marker for ovarian cancers—especially for clear cell carcinoma]. Nippon Sanka Fujinka Gakkai Zasshi, 1989. 41(9): p. 1341-7.

61. Nozawa, S., et al., [Clinical significance of galactosyltransferase associated with tumor (GAT), a new tumor marker for ovarian cancer—with special reference to the discrimination between ovarian cancer and endometriosis]. Gan To Kagaku Ryoho, 1994. 21(4): p. 507-16.

62. Paliouras, M., C. Borgono, and E. P. Diamandis, Human tissue kallikreins: The cancer biomarker family. Cancer Lett, 2007. 249(1): p. 61-79.

63. Paulick, R., et al., Clinical significance of different serum tumor markers in gynecological malignancies. Cancer Detect Prev, 1985. 8(1-2): p. 115-20.

64. Plebani, M., et al., Combined use of urinary UGP and serum CA 125 in the diagnosis of gynecological cancers. Anticancer Res, 1996. 16(6B): p. 3833-8.

65. Robertson, D. M., E. Pruysers, and T. Jobling, Inhibin as a diagnostic marker for ovarian cancer. Cancer Lett, 2007. 249(1): p. 14-17.

66. Rzymski, P., et al., [Evaluation of serum sICAM-1 amd CA-125 in patients with ovarian tumors—preliminary report]. Ginekol Poi, 2002. 73(11): p. 1090-5.

67. Sawada, M., et al., Immunosuppressive acidic protein in patients with gynecologic cancer. Cancer, 1984. 54(4): p. 652-6.

68. Scambia, G., et al., CA 15-3 as a tumor marker in gynecological malignancies. Gynecol Oncol, 1988. 30(2): p. 265-73.

69. Scambia, G., et al., Measurement of a monoclonal-antibody-defined antigen (90K) in the sera of patients with ovarian cancer. Anticancer Res, 1988. 8(4): p. 761-4.

70. Scholler, N., et al., Bead-based ELISA for validation of ovarian cancer early detection markers. Clin Cancer Res, 2006. 12(7 Pt 1): p. 2117-24.

71. Shan, L., L. Davis, and S. L. Hazen, Plasmalogens, a new class of biomarkers for ovarian cancer detection, in 55'th ASMS Annual Conference. 2007: Indianapolis, Ind.

72. Simon, I., et al., Evaluation of the novel serum markers B7-H4, Spondin 2, and DcR3 for diagnosis and early detection of ovarian cancer. Gynecol Oncol, 2007.

73. Simon, I., et al., B7-h4 is a novel membrane-bound protein and a candidate serum and tissue biomarker for ovarian cancer. Cancer Res, 2006. 66(3): p. 1570-5.

74. Simon, R., Development and evaluation of therapeutically relevant predictive classifiers using gene expression profiling. J Natl Cancer Inst. 2006. 98(17): p. 1169-71.

75. Skates, S. J., et al., Preoperative sensitivity and specificity for early-stage ovarian cancer when combining cancer antigen CA-125II, CA 15-3, CA 72-4, and macrophage colony-stimulating factor using mixtures of multivariate normal distributions. J Clin Oncol, 2004. 22(20): p. 4059-66.

76. Skates, S. J., et al., Pooling of case specimens to create standard serum sets for screening cancer biomarkers. Cancer Epidemiol Biomarkers Prev, 2007. 16(2): p. 334-41.

77. Sun, Z., et al., A protein chip system for parallel analysis of multi-tumor markers and its application in cancer detection. Anticancer Res, 2004. 24(2C): p. 1159-65.

78. Tas, F., et al., The value of serum bcl-2 levels in advanced epithelial ovarian cancer. Med Oncol, 2006. 23(2): p. 213-7.

79. Taylor, D. D., C. Gercel-Taylor, and S. A. Gall, Expression and shedding of CD44 variant isoforms in patients with gynecologic malignancies. J Soc Gynecol Investig, 1996. 3(5): p. 289-94.

80. Tosner, J., J. Krejsek, and B. Louda, Serum prealbumin, transferrin and alpha-1-acid glycoprotein in patients with gynecological carcinomas. Neoplasma, 1988. 35(4): p. 403-11.

81. Tsigkou, A., et al., Total inhibin is a potential serum marker for epithelial ovarian cancer J Clin Endochrin Metal), 2007.

82. Tsukishiro, S., et al., Preoperative serum thrombopoietin levels are higher in patients with ovarian cancer than with benign cysts. Eur J Obstet Gynecol Reprod Biol, 2005.

83. Vlahou, A., et al., Diagnosis of Ovarian Cancer Using Decision Tree Classification of Mass Spectral Data. J Biomed Biotechnol, 2003. 2003(5): p. 308-314.

84. Woong-Shick, A., et al., Identification of hemoglobin-alpha and -beta subunits as potential serum biomarkers for the diagnosis and prognosis of ovarian cancer. Cancer Sci, 2005. 96(3): p. 197-201.

85. Wu. S. P., et al., SELDI-TOF MS profiling of plasma proteins in ovarian cancer. Taiwan J Obstet Gynecol, 2006. 45(1): p. 26-32.

86. Xu, Y., et al., Lysophosphatidic acid as a potential biomarker for ovarian and other gynecologic cancers. Jama, 1998. 280(8): p. 719-23.

87. Yabushita, H., et al., Combination assay of CA125, TPA, IAP, CEA, and ferritin in serum for ovarian cancer. Gynecol Oncol, 1988. 29(1): p. 66-75.

88. Ye, B., et al., Proteomic-based discovery and characterization of glycosylated eosinophil-derived neurotoxin and COOH-terminal osteopontin fragments for ovarian cancer in urine. Clin Cancer Res, 2006. 12(2): p. 432-41.

89. Yu, J. K., et al., An integrated approach utilizing proteomics and bioinformatics to detect ovarian cancer. J Zhejiang Univ Sci B, 2005. 6(4): p. 227-31.

90. Yurkovetsky, Z. R., Serum Multimarker Assay for Early Detection of Ovarian Cancer, in 14'th International Molecular Medicine Tri-Conference. 2007: Moscone Norht Convention Center, San Fransisco, Calif.

91. Zhang, H., et al., Biomarker discovery for ovarian cancer using SELDI-TOF-MS. Gynecol Oncol, 2006. 102(1): p. 61-6.

92. Zhang, Z., et al., Three biomarkers identified from serum proteomic analysis for the detection of early stage ovarian cancer. Cancer Res, 2004. 64(16): p. 5882-90.

93. Zhao, C., et al., Circulating haptoglobin is an independent prognostic factor in the sera of patients with epithelial ovarian cancer. Neoplasia, 2007. 9(1): p. 1-7.

The invention claimed is:

1. An article of manufacture comprising a set of reagents to measure the levels of a panel of biomarkers in a specimen, wherein the panel of biomarkers comprise CA125, Apo A1, HE4, and FSH, and their measurable fragments, and wherein the set of reagents are bound to a solid support and specifically bind to said biomarkers.

2. The set of reagents of claim 1, wherein the reagents are binding molecules.

3. The set of reagents of claim 2, wherein the binding molecules are antibodies.

4. A test kit comprising the set of reagents of claim 1.

5. A multianalyte panel assay comprising the set of reagents of claim 1.

6. A method of predicting the likelihood of cancer in a subject, comprising: detecting the levels of biomarkers in a specimen using the set of reagents of claim 1, wherein a change in the levels of the biomarkers, as compared with a control group of patients who do not have cancer, is predictive of cancer in that subject.

7. The method of claim 6, wherein the cancer is ovarian cancer.

8. The method of claim 7, wherein a change in the relative levels of the biomarkers is determined.

9. The method of claim 7, wherein the specimen is selected from the group consisting of blood, serum, plasma, lymph, cerebrospinal fluid, ascites, urine and tissue biopsy.

10. The method of claim 7, wherein the ovarian cancer is selected from the group consisting of serous, endometrioid, mucinous, and clear cell cancer.

11. The method of claim 7, wherein the prediction of ovarian cancer includes a stage selected from the group consisting of Stage IA, IB, IC, II, III and IV tumors.

12. The method of claim 7, further comprising creating a report of the relative levels of the biomarkers.

13. The method of claim 12, wherein the report includes the prediction as to the presence or absence of ovarian cancer in the subject or the stratified risk of ovarian cancer for the subject, optionally by stage of cancer.

14. The method of claim 7, wherein the sample is taken from a subject selected from the group consisting of subjects who are symptomatic for ovarian cancer and subjects who are at high risk for ovarian cancer.

15. The method of claim 7, wherein the method has a sensitivity of at least about 85 percent and a specificity of at least about 85 percent.

16. The method of claim 15, wherein the sensitivity and specificity are determined for a population of women who are symptomatic for ovarian cancer and have ovarian cancer as compared with a control group of women who are symptomatic for ovarian cancer but who do not have ovarian cancer.

17. A method to assess the therapeutic efficacy of a cancer treatment, comprising: comparing the biomarker profiles in specimens taken from a subject before and after the treatment or during the course of treatment with a set of reagents according to claim 1, wherein a change in the biomarker profile over time toward a non-cancer profile or to a stable profile is interpreted as efficacy.

18. A method for determining whether a subject potentially is developing cancer, comprising: comparing the biomarker profiles in specimens taken from a subject at two or more points in time with a set of reagents according to claim 1, wherein a change in the biomarker profile toward a cancer profile, is interpreted as a progression toward developing cancer.

* * * * *